US009901246B2

(12) United States Patent
Whitmore, III

(10) Patent No.: US 9,901,246 B2
(45) Date of Patent: Feb. 27, 2018

(54) CYSTOSCOPY SYSTEM INCLUDING A CATHETER ENDOSCOPE AND METHOD OF USE

(71) Applicant: Verathon Inc., Bothell, WA (US)

(72) Inventor: Willet F. Whitmore, III, Longboat Key, FL (US)

(73) Assignee: Verathon Inc., Bothell, WA (US)

( * ) Notice: Subject to any disclaimer, the term of this patent is extended or adjusted under 35 U.S.C. 154(b) by 404 days.

(21) Appl. No.: 14/598,950

(22) Filed: Jan. 16, 2015

(65) Prior Publication Data

US 2015/0216403 A1 Aug. 6, 2015

Related U.S. Application Data

(60) Provisional application No. 61/936,063, filed on Feb. 5, 2014.

(51) Int. Cl.
| | | |
|---|---|---|
| *A61B 1/307* | (2006.01) | |
| *A61B 1/00* | (2006.01) | |
| *A61B 1/05* | (2006.01) | |
| *A61B 1/06* | (2006.01) | |

(Continued)

(52) U.S. Cl.
CPC .......... *A61B 1/307* (2013.01); *A61B 1/00082* (2013.01); *A61B 1/00096* (2013.01); *A61B 1/00114* (2013.01); *A61B 1/00119* (2013.01); *A61B 1/00181* (2013.01); *A61B 1/015* (2013.01); *A61B 1/05* (2013.01); *A61B 1/0676* (2013.01); *A61M 25/00* (2013.01)

(58) Field of Classification Search
CPC . A61B 1/307; A61B 1/00045; A61B 1/00011; A61B 1/00082; A61B 1/0096; A61B 1/05; A61B 1/00154; A61B 1/0676; A61B 1/00144; A61B 1/005; A61B 1/015; A61B 1/00119
See application file for complete search history.

(56) References Cited

U.S. PATENT DOCUMENTS

| | | |
|---|---|---|
| 5,855,549 A | 1/1999 | Newman |
| 6,461,294 B1 | 10/2002 | Oneda et al. |
| 6,530,881 B1 | 3/2003 | Ailinger et al. |

(Continued)

OTHER PUBLICATIONS

International Search Report for PCT/US2015/011897 dated Mar. 27, 2015.

*Primary Examiner* — Timothy J Neal
(74) *Attorney, Agent, or Firm* — Snyder, Clark, Lesch & Chung, LLP

(57) ABSTRACT

A system including catheter endoscope for deployment in the bladder of a patient to provide a visual display of the bladder's mucosal surface is disclosed. The catheter endoscope is an elongated member having an image acquisition component and an expandable positioning component. The catheter is deployed such that the expandable positioning component is in the bladder adjacent the bladder's neck with the image acquisition component held away from any portion of the mucosal surface. The image acquisition component is arranged to acquire a panoramic image of a sector of the mucosal surface of the bladder from the neck of the bladder to the mucosal surface of the bladder opposite the neck of the bladder and to be rotated about the axis along which the catheter is inserted to acquire an image of the entire mucosal surface of the bladder which is displayed on a monitor forming a portion of the system.

25 Claims, 8 Drawing Sheets

(51) Int. Cl.
    *A61B 1/015*    (2006.01)
    *A61M 25/00*   (2006.01)

(56) References Cited

U.S. PATENT DOCUMENTS

| | | |
|---|---|---|
| 6,599,237 B1 | 7/2003 | Singh |
| 6,994,667 B2 | 2/2006 | Singh |
| 8,289,381 B2 | 10/2012 | Bayer et al. |
| 8,360,968 B2 | 1/2013 | Hadani |
| 8,460,182 B2 | 6/2013 | Ouyang et al. |
| 8,622,893 B2 | 1/2014 | Mathieu |
| 2007/0177008 A1 | 8/2007 | Bayer et al. |
| 2009/0318797 A1 | 12/2009 | Hadani |
| 2012/0053485 A1 | 3/2012 | Bloom |
| 2013/0331824 A1 | 12/2013 | Kim |

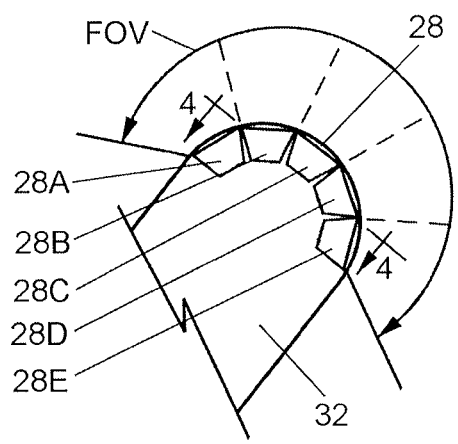
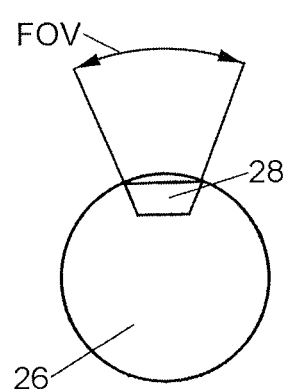
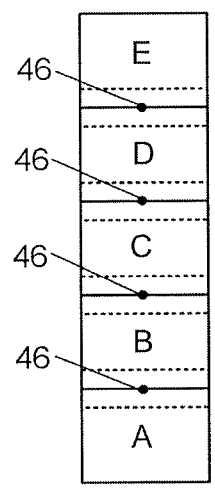
Fig. 3   Fig. 4   Fig. 5
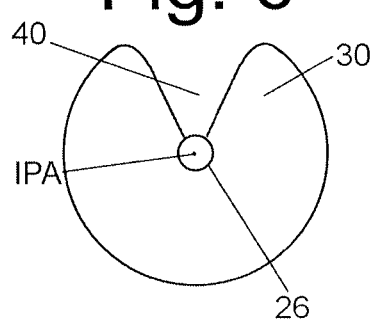
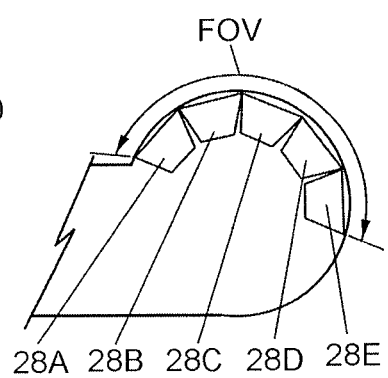
Fig. 6   Fig. 7
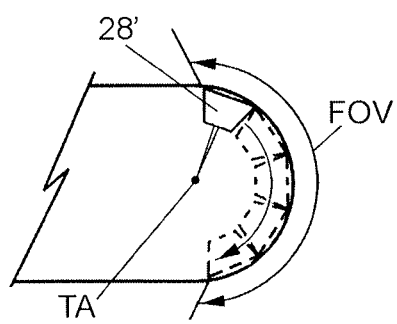
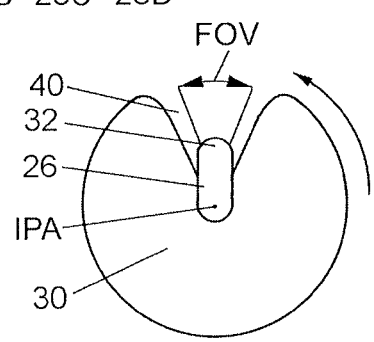
Fig. 8   Fig. 9

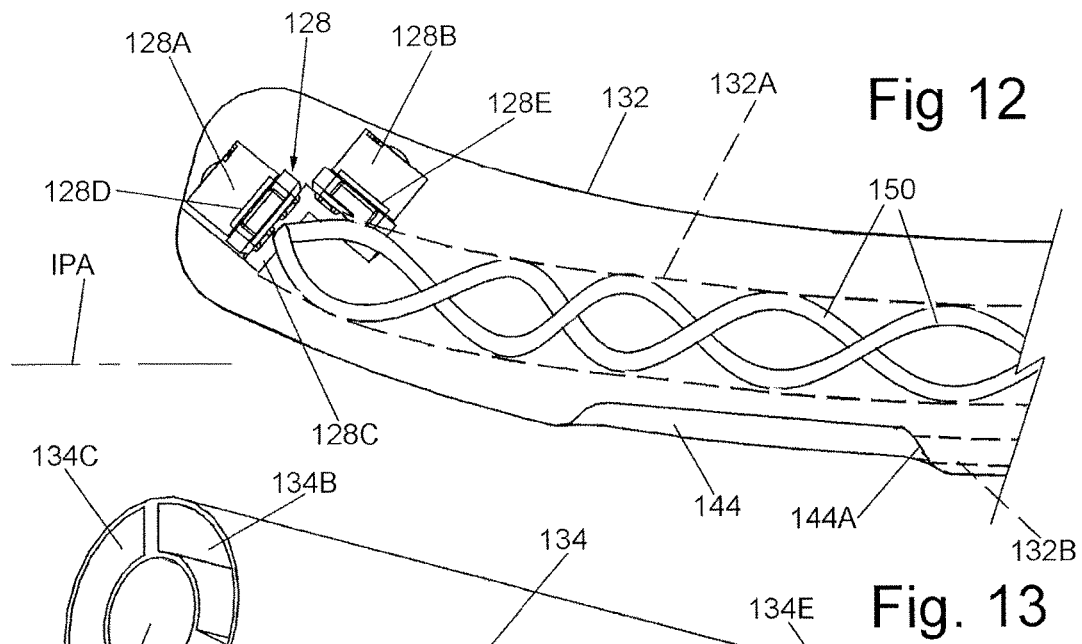
Fig 12
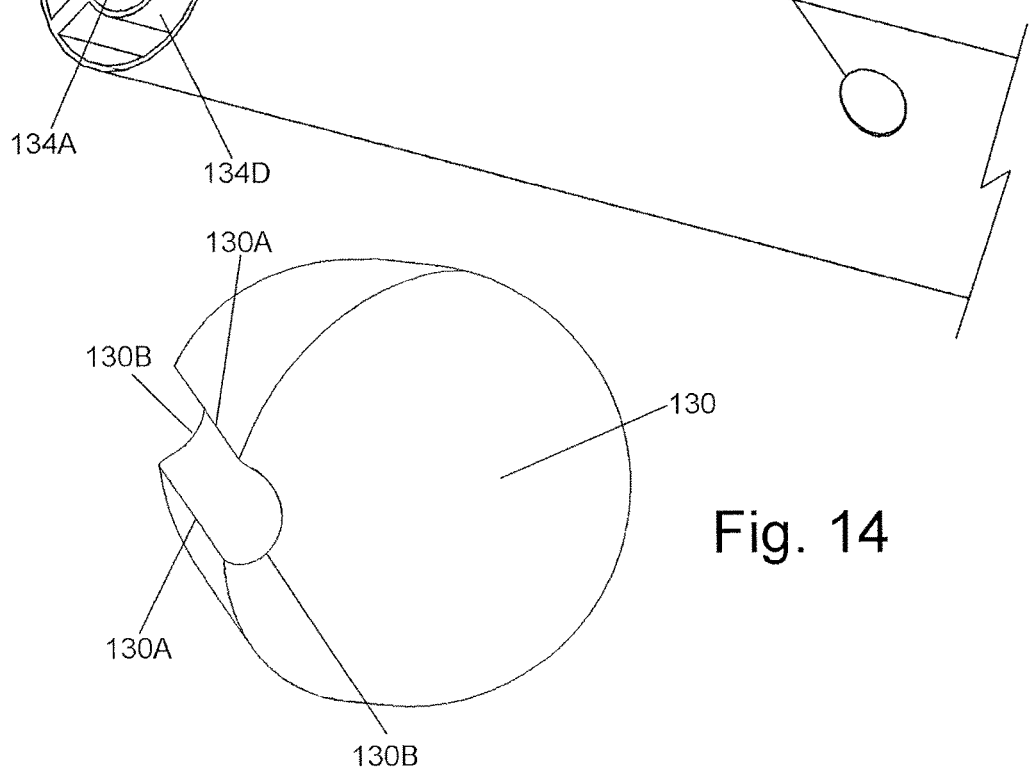
Fig. 13
Fig. 14

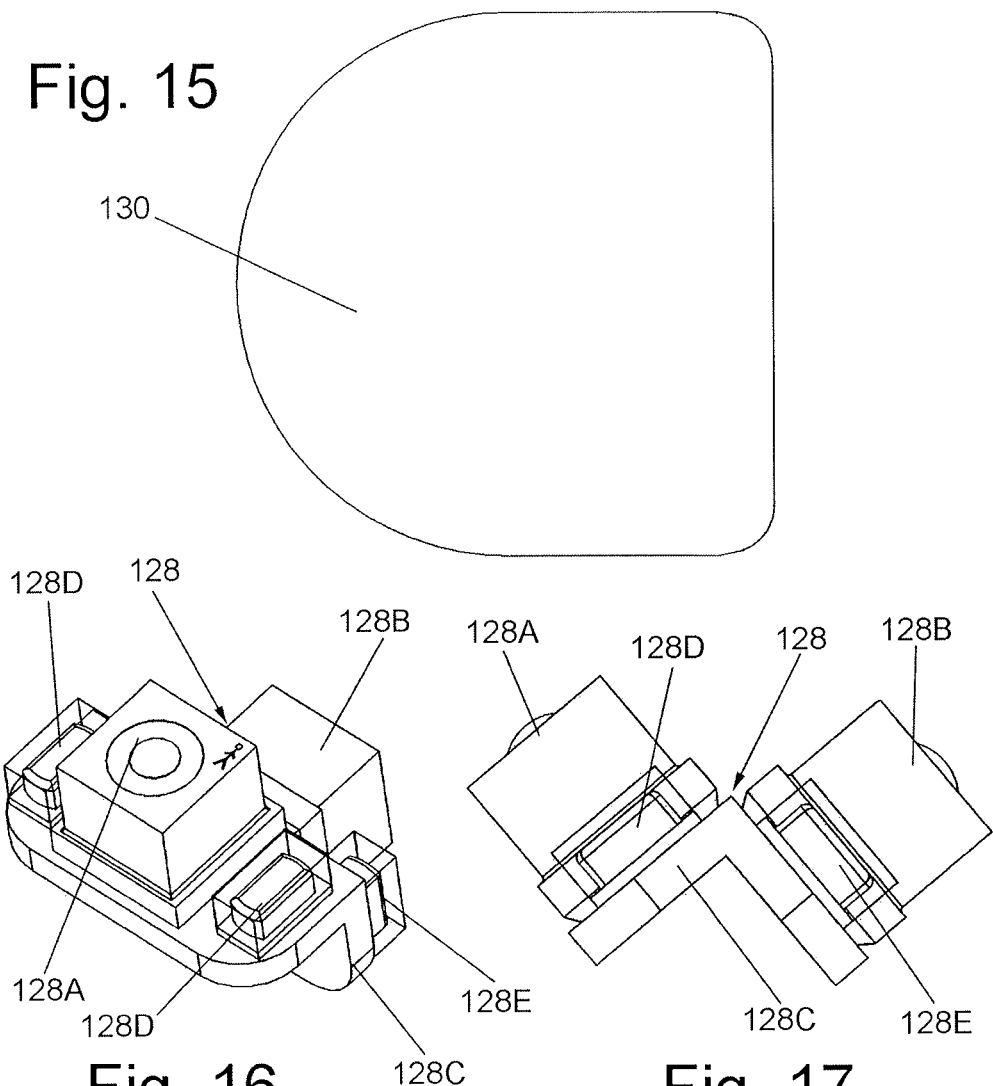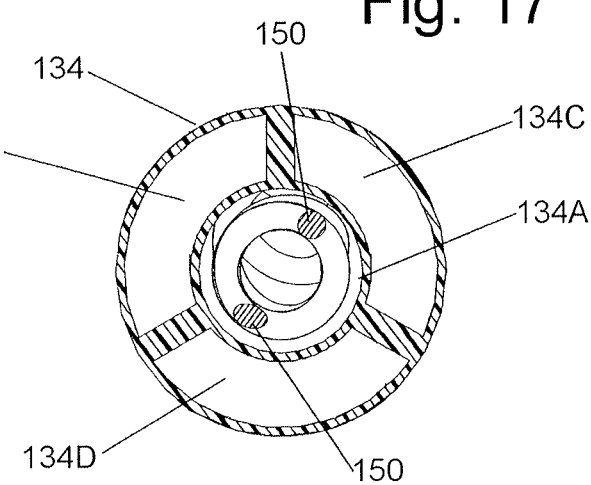

CYSTOSCOPY SYSTEM INCLUDING A CATHETER ENDOSCOPE AND METHOD OF USE

CROSS-REFERENCE TO RELATED APPLICATIONS

This utility application claims the benefit under 35 U.S.C. § 119(e) of Provisional Application Ser. No. 61/936,063 filed on Feb. 5, 2014 entitled Cystoscopy System Including A Catheter Endoscope And Method Of Use, whose entire disclosure is incorporated by reference herein and which is assigned to the same assignee as the subject invention.

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

FIELD OF THE INVENTION

This invention relates generally to medical instruments and more particularly to systems including catheter endoscopic instruments for imaging a hollow anatomic structure, such as the bladder, of a patient.

BACKGROUND OF THE INVENTION

Diagnostic (non-operative) cystoscopy, the simple endoscopic examination of the bladder and urethra, is a fundamental part of the urologic diagnostic work-up. Heretofore cystoscopy has been limited to physician/urologists using specialty specific endoscopes called cystoscopes. All current cystoscopes are either straight, and require exchanging rigid fiber-optic lenses with different viewing angles in the axis of the instrument, or flexible with manual mechanical, off axis, directional control of the tip optics that have a fixed field of view. Complete examination is achieved by filling (expanding) the urethra and bladder with clear fluids while the operator visually guides the instrument and using a combination of angular and longitudinal manipulation (plus the exchange of differently angled lenses in the case of rigid instruments) to visualize the entirety of the urethra and bladder's mucosal surface. These instruments all have a channel for infusion and withdrawal of water or clear saline solutions, optics for light and image transmission, and may also have additional channels for fluid drainage and passage for surgical instruments. Cystoscopes may come with optics for direct visualization by the operator, or, increasingly, with a built in camera or a method for camera attachment for real time viewing of digital images on a monitor, and possibly, still or video photography. Cystoscopes have become highly developed for physician use over the past 100 years, with major improvements in lighting, optics (image brightness, color control and resolution) and procedural versatility. In general, they are re-usable and have been persistently expensive to buy, re-process and maintain. What also has been constant is the need for an experienced physician operator and the simple anatomy that requires visual examination.

There are at least six barriers to reducing the global time and expense of cystoscopic examination. They are: the requirement for a physician operator; the skill and time it takes to manipulate the optics at the instrument tip for complete visualization of the mucosal surfaces of the bladder and urethra; the general requirement for a room that allows for equipment setup, storage and maintenance, and at least for the rigid instruments, a cystoscopy table for performance; the cleaning and re-sterilization requirement before every use; and the need for advance scheduling to make sure that the equipment, room and physician are coordinated.

Vision Sciences, Inc. offers disposable sheaths under the trademark Endosheath® (VSCI) for a flexible cystoscope in an attempt to escape the re-processing/sterilization step and have patents relating to disposable sheathes for endoscopes. See for example, U.S. Pat. Nos. 6,530,881; 6,461,294; and 8,360,968.

Cleaning and re-sterilization is an accepted bother that is also not 100% reliable or 100% safe. There are many case reports of patients developing a urinary tract infection and even sepsis from incorrectly processed or broken cystoscopes. This is the basis for the pursuit of solutions by companies like Vision Sciences, Inc. While such protective arrangements are somewhat suitable for their intended purposes they have not achieved widespread acceptance because of the added expense of the sheath. Moreover, cystoscope cleaning and reprocessing are still required. The use of a sheath reduces the functionality of the instrument.

Other endoscopes have been made to be disposable after a number of uses. One example is a device offered by Boston Scientific under the trademark Spyglass®. It employs a disposable fiber-optic cable and lens that connects to a reusable analog camera and light source. It has a flexible, mechanically manipulated tube for delivery of the cable and other medical instruments that is also disposable.

Axess Vision Technology, of Tours, France, offers a re-usable handle containing the electronics and fluid input port that is then attached to a disposable conduit and optical tip. See U.S. Pat. No. 8,622,893. This arrangement allows the user to avoid the re-sterilization requirement for the portion of the equipment that contacts the patient.

Other disposable endoscopes can be referred to as being of a "chip on a stick" variety. These are semi-rigid instruments containing wires for electricity and data transmission that have lighting elements and a digital camera chip (e.g., CCD, CMOS, etc.) on the tip. One example is a hysteroscope offered by EndoSee Corporation and disclosed in U.S. Pat. No. 8,460,182. That instrument is arranged for insertion into the uterus under direct visual control. The tip is angled so that complete viewing of a narrow viscus is possible with longitudinal movement plus rotation, and minimal angulation of the main longitudinal axis.

All of these above described prior art devices are designed for use by highly skilled and vetted operators and essentially mimic the standard reusable endoscopes as closely as possible while pursuing the goals of eliminating or reducing reprocessing costs and improving sterility.

Percuvision LLC has developed a catheter that contains optics looking forward from the tip to facilitate catheter placement and directly manage any obstructions to placement as placement is proceeding. The self-steering facility of the catheter also enables a less skilled operator to introduce it through the passage and into a body cavity. It uses a symmetrical annular balloon like a typical Foley catheter for retention once located in a desired cavity. Once in position the catheter may be used for drainage or as a sheath or conduit for additional instrumentation such as endoscopes.

U.S. Pat. Nos. 6,994,667 and 6,599,237 and published application US2009/0318797 appear to relate to the Percuvision catheter.

U.S. Pat. No. 8,289,381, assigned to Avantis Medical Systems, Inc. discloses an endoscope assembly in the form of an endoscope with a first imaging sensor and a first light source aimed in a forward direction from the distal end of the endoscope, and a rear-viewing imaging device with a curved link configured to extend beyond the distal end of the endoscope. The rear-viewing imaging device has a second imaging sensor and a second light source which face the first imaging sensor. The second imaging sensor and the second light source are disclosed as being on when the first imaging sensor and the first light source are off, and vice-versa. The imaging sensors are stated as possibly having adjacent or overlapping viewing areas or to provide different views of the same area. It is stated that preferably, the second imaging sensor provides a retrograde view of the area, while the first imaging sensor provides a front view of the area. However, the second imaging sensor could be oriented in other directions to provide other views, including a forward view and views that are substantially parallel to the axis of the first imaging sensor.

Notwithstanding the foregoing prior art a need still exists for an instrument which can be used by less skilled personnel than personnel typically conducting an endoscopic examination, does not require time consuming and risky cleaning and sterilization reprocessing, leaves no questions regarding sterility, and yet can provide a medically viable image of the urethra and entire mucosal surface of the bladder with minimal manipulation by the user and which is simple in construction and low in cost. The latter features enabling it be used on a one-time basis and then discarded.

The subject invention addresses these needs among others. For example, the subject invention makes use of the self-guiding characteristics of a Foley catheter for placement, but goes much farther by also eliminating the requirements for a skilled operator (e.g., physician) for performing complete mucosal visualization (i.e. complete cystoscopy). Thus the system and instrument of the subject invention can be used by personnel suitable for deploying a conventional Foley catheter (e.g., nurses or physician assistants). It eliminates the risks of inadequate cleaning and sterilization. It also eliminates any requirement for complex tip manipulation to achieve complete visualization, while also obviating the need for a specialty work area or venue. Moreover, it greatly simplifies scheduling logistics.

All references cited and/or identified herein are specifically incorporated by reference herein.

SUMMARY OF THE INVENTION

One aspect of this invention is a catheter endoscope for a cystoscopy system. The catheter endoscope is configured for deployment in the body of a patient to provide an image of the mucosal surface of the patient's urethra and bladder for display on an externally located display device and comprises an elongated member, an image acquisition component and an expandable positioning component. The elongated member has a distal end portion at which the image acquisition component is located. The expandable positioning component is located proximally adjacent the distal end portion. The distal end portion and the expandable positioning component are arranged to be deployed in the bladder by moving the elongated member and the expandable positioning component through the urethra and the neck of the bladder along an insertion path towards the mucosal surface of the bladder opposite the neck of the bladder whereupon the distal end portion is located at a desired longitudinal position along the insertion path and the expandable positioning component is located adjacent the neck of the bladder. The insertion path has a longitudinal axis. The expandable positioning component is configured to be expanded to hold the distal end portion of the elongated member in the desired longitudinal position and away from any portion of the mucosal surface of the bladder. The expandable positioning component has a window therein exposing a portion of the mucosal surface of the bladder contiguous with the neck of the bladder. The image acquisition component is configured to acquire a panoramic image of a sector of the mucosal surface of the bladder from the neck of the bladder to the mucosal surface of the bladder opposite the neck of the bladder within a predetermined angular field of view extending radially outward from the longitudinal axis of the insertion path. The window is located within the predetermined angular field of view so as to expose a portion of the mucosal surface of the bladder contiguous with the neck of the bladder within the sector of the mucosal surface. The elongated member is configured to be rotated about the longitudinal axis of the insertion path while the distal end of the elongated member is in the desired longitudinal position whereupon the image acquisition component acquires a video image of the mucosal surface of the bladder from the neck of the bladder to the mucosal surface of the bladder opposite the neck of the bladder to produce an electrical signal representative of the image of the entire mucosal surface of the bladder. The catheter endoscope is configured to provide the electrical signal to the externally located display device.

Another aspect of this invention is a method of providing an image of the mucosal surface of the bladder of a patient. The method comprises providing a catheter endoscope comprising an elongated member, an image acquisition component, and an expandable positioning component. The elongated member has a distal end portion at which the image acquisition component is located. The expandable positioning component is located proximally adjacent the distal end portion. The elongated member and the expandable positioning component are introduced through the urethra of the patient and the neck of the bladder along an insertion path having a longitudinal axis towards the mucosal surface of the bladder opposite the neck of the bladder, whereupon the distal end portion is located at a desired longitudinal position along the insertion path and the expandable positioning component is located adjacent the neck of the bladder. The expandable positioning component is expanded to hold the distal end portion of the elongated member in the desired longitudinal position and away from any portion of the mucosal surface of the bladder. The expandable positioning component has a window therein exposing a portion of the mucosal surface of the bladder contiguous with the neck of the bladder.

The image acquisition component is operated to acquire a panoramic video image of a sector of the mucosal surface of the bladder from the neck of the bladder to the mucosal surface of the bladder opposite the neck of the bladder within a predetermined angular field of view extending radially outward from the longitudinal axis of the insertion path. The window of the expandable positioning member is located within the predetermined angular field of view so as to expose a portion of the mucosal surface of the bladder contiguous with the neck of the bladder within the sector. The elongated member is rotated about the longitudinal axis of the insertion path while the distal end of the elongated member is in the desired longitudinal position to produce an electrical signal representative of the entire mucosal surface of the bladder. That signal is provided to an externally located display device.

DESCRIPTION OF THE DRAWING

FIG. 3 is an enlarged sectional view of the distal end portion of the catheter endoscope shown within the area designated by the numeral "3" in FIG. 2 and illustrating the combined longitudinal panoramic field of view (FOV), back-to-front, produced by the image acquisition component (plural sensors) located therein to enable the catheter endoscope to acquire an image of a sector of the of the mucosal surface of the bladder from the neck of the bladder to the mucosal surface of the bladder opposite the neck of the bladder;

FIG. 4 is an enlarged sectional view of distal end portion (tip) of the catheter endoscope taken in the direction of line 4-4 of FIG. 3 and showing the angular field of view (FOV) extending radially outward from the longitudinal axis of the insertion path produced by each of the sensors of the image acquisition component;

FIG. 5 is a plan view of a sector of the mucosal surface of the bladder from the neck of the bladder to the mucosal surface of the bladder opposite the neck of the bladder acquired by the sensors of the image acquisition component shown in FIG. 3;

FIG. 6 is a slightly reduced sectional view taken along line 6-6 of FIG. 2;

FIG. 7 is an enlarged sectional view of the distal end portion (tip) of an alternative exemplary embodiment of the catheter endoscope of FIG. 1;

FIG. 8 is an enlarged sectional view of the distal end portion (tip) of still another alternative exemplary embodiment of the catheter endoscope of FIG. 1;

FIG. 9 is a slightly reduced sectional view taken along line 9-9 of FIG. 2;

FIG. 12 is an enlarged side elevation view of the distal end of the catheter endoscope shown in FIG. 10 and showing the location of its image acquisition component located therein;

FIG. 13 is an enlarged isometric view of the distal end portion of a tubular component forming a portion of the catheter endoscope shown in FIG. 10;

FIG. 14 is an isometric view of one of the two positioning balloons forming a portion of the catheter endoscope shown in FIG. 10;

FIG. 15 is a top plan view of the positioning balloon shown in FIG. 14;

FIG. 16 is an enlarged isometric view of the image acquisition component shown in FIGS. 11 and 12;

FIG. 17 is a side elevation view of the image acquisition component shown in FIG. 16;

FIG. 18 is an enlarged sectional view taken along line 18-18 of FIG. 11;

DETAILED DESCRIPTION OF THE PREFERRED EMBODIMENT

Figure 1:
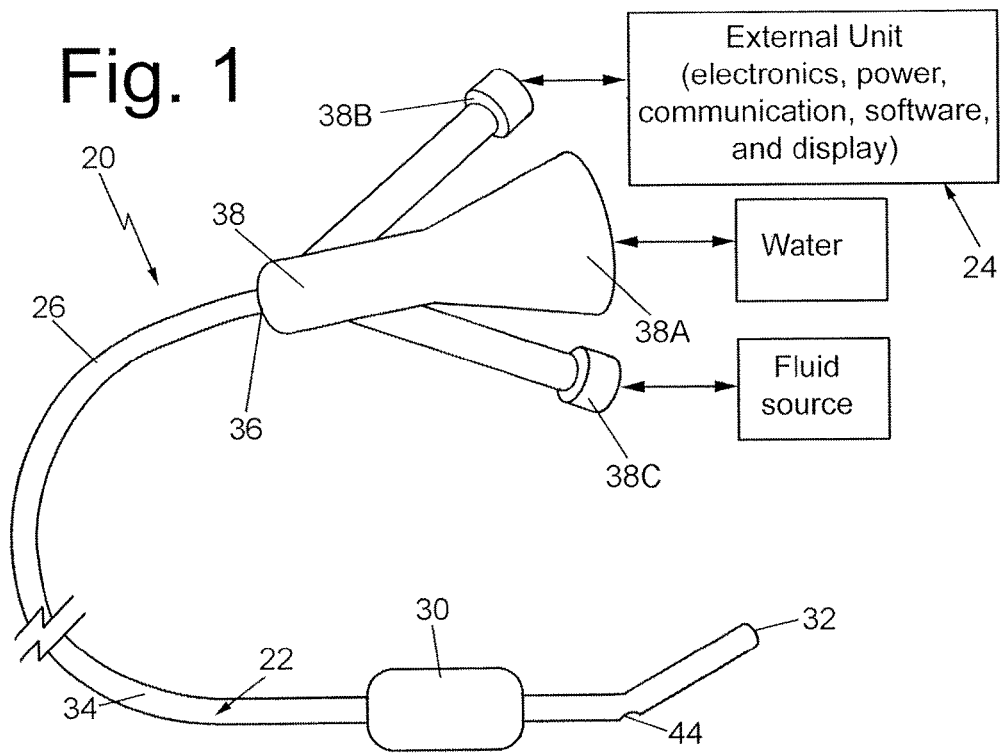
FIG. 1 is an elevation view of one exemplary embodiment of a medical system making use of one exemplary catheter endoscope constructed in accordance with this invention.

Referring now to the various figures of the drawing wherein like reference characters refer to like parts, there is shown in FIG. 1 an instrument system 20 constructed in accordance with this invention for enabling one to conduct a cystoscopic examination of the bladder 10 of a patient. The system 20 basically comprises a catheter endoscope (which may also be referred to as a "cystoscopy catheter") 22 and an external unit or console 24 (whose housing isn't shown in the interest of drawing simplicity). The cystoscopy catheter 22 shown in FIG. 1 constitutes one exemplary embodiment of a number of catheter endoscopes that can be constructed in accordance with the teachings of this invention. To that end, in FIG. 10 there is shown another instrument system 120 constructed in accordance with this invention for conducting a cystoscopic examination of a patient's bladder. The system 120 also basically comprises a catheter endoscope 122 and an external unit or console 24. The same external unit or console 24 can used in both systems 20 and 120, although there may be some differences in the electronics of each of those systems.

The exemplary cystoscopy catheters 20 and 120 are similar in many respects and different in others. For example, insofar as similarities are concerned, both catheters 22 and 122 are preferably a supple, single use, pre-sterilized, disposable catheters somewhat mechanically similar to a standard Foley (balloon) urethral catheter, but each includes internal optics for doing cystoscopy. The external unit 24 will also be described later. Suffice it for now to state that it serves to control the operation of the catheters 22 and 122 and receive signals therefrom to provide a visual image of a portion or the entirety of the mucosal surface of the patient's bladder and/or urethra on a video monitor or display (which forms a portion of the external unit or may be a separate unit).

Unlike catheter endoscope 122, the catheter endoscope 22 includes an image acquisition component which is arranged to be pivoted with respect to the distal end of the catheter to provide a composite image of the entire mucosal surface of the bladder. In contradistinction, the catheter endoscope 122 includes an image component that is fixed with respect to the distal end of the catheter, but still can provides an image of the entire mucosal surface of the bladder or any portion thereof. The catheter endoscope 122 constitutes a preferred exemplary embodiment of this invention for various reasons to be appreciated from the discussion to follow. However, before discussing that preferred embodiment of the invention, a discussion of the catheter endoscope 22 is in order.

To that end, turning now to FIGS. 1-3 the details of the exemplary embodiment of the cystoscopy catheter 22 will now be described. That device basically comprises an elongated catheter-like member 26, an image acquisition component 28 (FIG. 3), and an expandable positioning component 30. The elongated member 26 has a distal end portion or tip 32, and intermediate portion 34 and a proximally located portion 36 terminating in a coupling 38. In accordance with one exemplary embodiment of the invention the elongated member may be a standard length (e.g., about 40 cm overall), single use, pre-sterilized, flexible urinary catheter of approximately 20 French size or less (=<7 mm diameter) with at least one through-channel or lumen (not shown) having a distinct entry port at the outside end that allows for the infusion or drainage of liquid. This channel may have a dual function as a passage for a stylet used to assist in catheter placement if certain anatomic abnormalities (such as urethral stricture) are present.

The image acquisition component 28 is located in the tip 32 and arranged to acquire an image of the mucosal surface of the bladder at which it is aimed. In the exemplary embodiment shown in FIG. 1, the tip is a Coude tip, i.e., it extends at an acute angle (e.g., 20 degrees) to the longitudinal axis of the intermediate portion 34. The expandable positioning component of the exemplary embodiment of FIG. 1 is in the form of an inflatable balloon. The balloon 30 is located proximally adjacent the tip 32 and as shown in FIG. 2 is arranged when inflated to engage the mucosal surface 12 of the bladder 10 adjacent the neck 14 of the bladder. The balloon 30 is similar in construction to that of a conventional Foley catheter, except that it is not of an annular shape extending about the entire periphery of the elongated member 26 as would be the case with a Foley catheter. Rather, as seen in FIG. 6, the balloon 30 includes a window 40 which exposes a portion of the mucosal surface 12 adjacent the neck of the bladder when the balloon is in place and inflated like shown in FIGS. 2 and 6. This facilitates imaging of the bladder's neck, as will be described later. The elongated member 26 includes a channel or lumen in communication with the interior of the balloon and also with a Luer type valve 38C forming a portion of the coupling 38 to enable a fluid, e.g., water, to be introduced into the balloon to fill it and thus cause it to expand.

Figure 2:
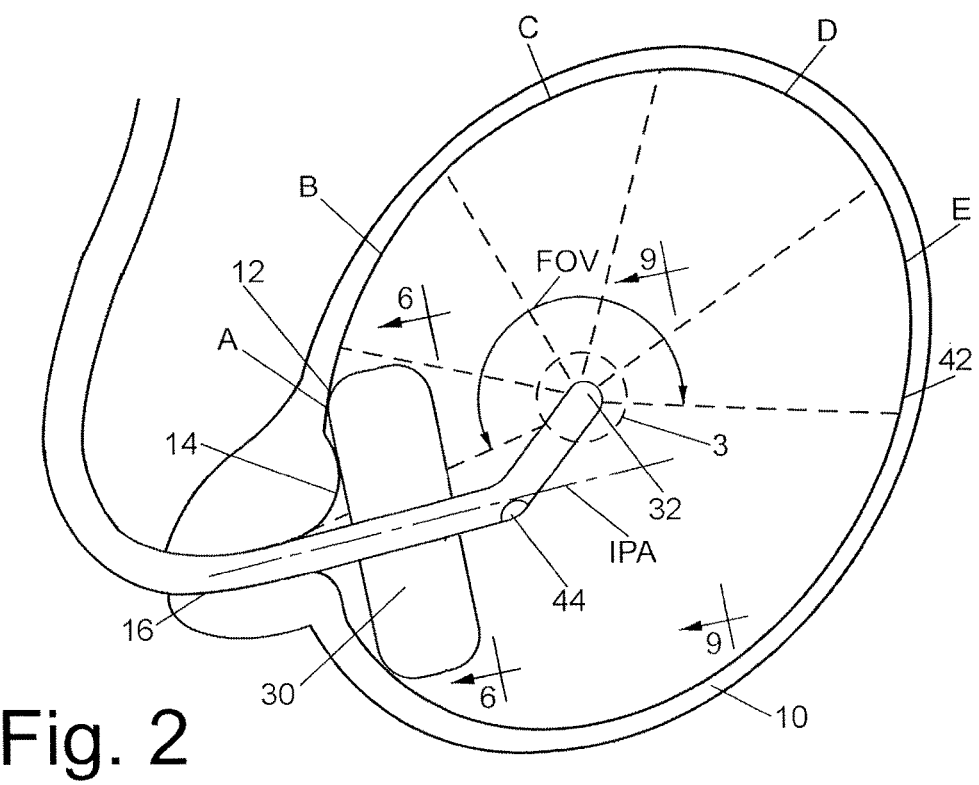
FIG. 2 is an illustration of a portion of the catheter endoscope of FIG. 1 shown in typical use within the bladder of a patient (in this case a male), wherein the catheter endoscope is deployed in the patient along a longitudinally extending insertion path through the urethra and the neck of the bladder.

The catheter 22 is introduced into the bladder 10 via an insertion path having a longitudinal axis IPA (FIG. 2). The insertion path extends through the urethra 16 and the neck 14 of the bladder and has a longitudinal axis IPA which extends from the neck 14 of the bladder to the portion 42 of the mucosal surface of the bladder directly opposite the neck of the bladder. The catheter 22 is constructed and arranged to be inserted to a desired longitudinal position along the axis IPA wherein the tip 32 is spaced away from any portion of the mucosal surface with the proximal surface of the balloon 30 is in abutment with the neck of the bladder, as shown in FIG. 2. This tip position is referred to as the 'desired longitudinal position" and in that position the tip is generally centered within the filled bladder. In order to enable viable imaging of the mucosal surface of the bladder by the image acquisition component 28 the catheter 22 is constructed to enable it to introduce sterile water into the bladder to fill the bladder. In this regard, the catheter includes a channel or lumen (not shown) extending therethrough and terminating at an open port 44 (FIGS. 1 and 2) in fluid communication with the interior of the bladder 10 adjacent the tip. That channel or lumen terminates at a valve-less, dilated opening 38A forming a portion of the coupling 38 for plugging in a friction type cone shaped connector (not shown) to a fluid source, e.g., a bag of sterile water on an elevated IV pole) for filling of the bladder. Thus, with such an arrangement the sterile water can flow under the force of gravity from the bag, through the coupling portion 38A, through the channel or lumen in the catheter and out through the port 44 into the bladder.

In accordance with one preferred embodiment of the invention, such as that shown in FIGS. 1 and 3, the image acquisition component comprises a plurality of imaging sensors 28A, 28B, 28C, 28D and 28E. In this embodiment each sensor is in the form of a CCD chip, a CMOS chip, or any other suitable electronic imaging component. The individual sensors are oriented to produce a combined panoramic field of view (FOV) extending longitudinally, i.e., along the longitudinal axis IPA for at least 180 degrees. This arrangement provides a panoramic image of a sector of the mucosal surface from the neck of the bladder to a point on the mucosal surface opposite the neck of the bladder within a predetermined angular field of view extending radially outward from the longitudinal axis of the insertion path. The predetermined angular field of view is shown in FIGS. 4 and 9. As can be seen in FIG. 9, the predetermined angle of view FOV of each sensor is aligned with the window 40 of the balloon so that the balloon does not obscure or interfere with imaging of the mucosal surface adjacent the neck of the bladder.

Moreover, each sensor 28A-28E is oriented so that its longitudinal field of view is directed in a respective direction such that the composite field of view is greater than 180 degrees. Thus, when the tip 32 of the catheter is in the position shown in FIG. 2 the longitudinal field of view of the image acquisition component 28 will extend from the neck of the bladder to at least the portion 42 of the mucosal surface. In fact, in the embodiment shown the FOV will extend slightly beyond the mucosal portion 42, e.g., the FOV will encompass 200 degrees. To that end, in the exemplary embodiment shown in FIGS. 1-3 the longitudinal field of view of each sensor is at approximately 40 degrees, while the angular field of view is approximately 45 degrees. The composite image thus acquired by the sensors 28A-28E is a strip such as illustrated in FIG. 5. In particular, the image acquired by the sensor 28A is designated as "A" in FIGS. 2 and 5, while the image acquired by the sensor 28B is designated as "B", the image acquired by the sensor 28C is designated as "C", the image acquired by the sensor 28D is designated as "D", and the image acquired by the sensor 28E is designated as "E" in those figures.

As will be appreciated by those skilled in the art the angular field of view of each of the sensors is not critical since the catheter 22 is arranged to be rotated about the longitudinal insertion axis IPA through an arc of at least 360 degrees while its tip 32 is in the desired longitudinal position along that axis to provide a composite image of the entire mucosal surface of the bladder. Moreover, the longitudinal field of view of each of the sensors making up the image acquisition unit will depend upon the number of sensors used so that the composite longitudinal field of view is at least 180 degrees. For example, if only three sensors are used, each should have a longitudinal field of view of at least 60 degrees, and preferably slightly more.

It should be noted that in practice the respective fields of view of each of the immediately adjacent sensors 28A-28E will overlap each other as shown by the dotted lines in FIG.

5 to provide a desired depth of field to viably image the mucosal surfaces at which the respective sensors are aimed. In particular, the field of view A of the sensor 28A overlaps the field of view B of the sensor 28B, the field of view B of the sensor 28B overlaps the field of view C of the sensor 28C, the field of view C of the sensor 28C overlaps the field of view D of the sensor 28D, and the field of view D of the sensor 28D overlaps the field of view E of the sensor 28E. In order to register the fields of view of each of those sensors so that the composite field of view will be accurate and representative of the mucosal surface imaged, the catheter 22 may include a laser (not shown) arranged to provide a laser beam to respective portions of the fields of view where they overlap to thereby produce respective points of reference or registration markers 46 thereat. Software in the system may utilize the fields imaged by each sensor (which includes the registration markers) to digitally process the electrical signals representative of the imaged fields register or stitch those fields together (e.g., to "edge-match" them) to form the desired composite image. Thus, with the system of this invention the user can view a portion or all of the mucosal surface may be seamless and accurate. Other, pure software pixel image analysis type, approaches to image registration may also be used.

While not shown in the drawing (in the interest of drawing simplicity) the catheter 22 preferably includes means for illuminating the interior of the bladder within the field of view of the image acquisition component 28. That illumination means can take any form, e.g., it may consist of one or more optic fibers, one or more LEDs, one or more lenses and/or mirrors or any combination thereof.

The acquisition of the image of the entire mucosal surface of the bladder is accomplished by rotating the cystoscopic catheter 22 about the axis IPA of the insertion path once the catheter is in the desired longitudinal position shown in FIG. 2. This action is accomplished by manipulating the proximally extending portion of the catheter so that the portion of the catheter within the bladder, including the balloon 30, rotates about the axis IPA. In FIG. 9 there is shown an end view of the tip of the catheter shown being rotated about that axis in the counterclockwise direction represented by the curved arrow. Since the balloon 30 rotates as a unit with the elongated member 26 about the axis IPA, the window 40 of the balloon will rotate simultaneously with the rotation of the image acquisition component, e.g., the sensors, at the tip 32 to ensure that the mucosal surface at neck of the bladder will not be obscured by the balloon at any point during the 360 degree rotation of the catheter about that axis.

As can be seen in FIG. 1, the coupling 38 includes a portion 38B including a plug which is arranged to be connected to a cable (not shown) from the external unit 24 to carry the signals, power, etc., to and from the catheter 22. If desired, the signals provided from the catheter's sensors may be provided via electrical conductors (not shown) extending through the coupling portion 38B and its associated cable, or such signals may be transmitted wirelessly to the unit 24.

In any case, the unit 24 includes a video monitor for visually displaying video images acquired by the catheter 22. Those images may be of the entire mucosal surface of the bladder, the urethra or any portion of either. Moreover, the images may be displayed as still images, if desired. The unit also functions as a video recorder with the ability to display the recorded data from each imaging sensor at a later time in any format desired by the reviewer. Thus the images may be reviewed as a panoramic movie, as a movie from each individual camera, as still panoramic images from selected sectors obtained during catheter rotation or as individual sector camera images. To that end, the unit 24 includes various electronic circuitry and components, e.g., a microprocessor, fluid management components, sensor monitors and software to assist with the examination and for controlling the operation of the various components of the system and reviewing the image data. Electric power for the unit 24 may be by means of a conventional power cord. Alternatively, or in addition, the unit 24 may include an on-board power supply, e.g., a battery. If desired, the unit may also include video recorder. An alternative for wireless data transmission from the catheter 22 to the monitor 24 may be in the form of a small power supply and wireless transmitter unit (not shown) that has a receptacle for receipt of the electrical plug 38B of the catheter.

The unit 24 also may be arranged to control and monitor the volume of fluid provided to the balloon 30, thereby controlling separation of the catheter distal end (tip) off (away from) the mucosal surface of the bladder once the catheter is through the urethra and correctly located in the bladder as shown in FIG. 2. The unit 24 is arranged control of the optics, such as the intensity of the light provided by an illumination source in the catheter, and the focus and/or selection of the image acquisition component 28.

The catheter 22 may also include position sensors incorporated in or near the tip and a laser rangefinder. An additional channel, which is blind-ending, may be provided in a segment of the catheter that does not enter the patient, for forming a self-sealing receptacle. This channel with the sealed end may receive a plug-in removable stylet that may communicate with power, lighting, data cables, camera(s) and/or sensors near the tip. Also, batteries may be embedded in the catheter wall and connected to illumination means and/or the image acquisition component. AC or DC power and data communication are supplied via wiring incorporated in the catheter (through a conduit or embedded during extrusion) that leads to the plug at portion 38B or to one or more external connector(s) (not shown) in plug form or in the just described self-sealing receptacle. If a powered stylet is used, it may have a substantial handle to contain a power supply and have wireless capability. It may be single use or reusable. The stylet may be shaped for insertion into the flexible catheter either before or after the catheter is sterilely inserted into the bladder. An alternative mechanical stylet also may be used in the main fluid channel of the catheter as a simple semi-rigid stiffener to aid in initial catheter insertion. It may temporarily fill the fluid irrigation channel and have a leading filiform shape that extends forward of the catheter tip for guidance or positioning purposes.

As shown in FIGS. 1 and 2 the catheter may have a Coude (angled) tip 32 or that tip may be of different shape. For example, as shown in FIG. 7, the tip 32' may be bulbous or spherical and may be concentric with the axis IPA or may be off-set therefrom like shown in FIG. 7. All of such tips are arranged to provide a backward looking sensor or camera. In lieu of using multiple sensors to provide a composite field of view, like the embodiment of FIGS. 1-3 and 7, the image acquisition component may be in the form of a single sensor or camera, which is arranged to be rotated to various positions so as to result in the composite longitudinal field of view like that produced by the plural sensors of FIGS. 1-3 and 7. That alternative exemplary arrangement is shown in FIG. 8, wherein a single sensor 28' is mounted for rotation about a transverse axis TA extending perpendicularly to the longitudinally extending insertion axis IPA.

It is anticipated that but for the inclusion of the expandable positioning component 30 the tip 32 of the catheter 22 may not routinely end up in a position in the bladder that is ideal for panoramic viewing of the entire mucosal surface at all angles of rotation of the catheter. For example, the tip 32 could end up resting in contact with the posterior wall of the bladder. The optics, light distribution and sensor, rely on a clear fluid interface and adequate separation from the mucosal surface for optimal viewing. This is where the expandable positioning component, e.g., the balloon 30, assists by holding the catheter in the desired longitudinal position. In this regard, inflating the balloon will be useful for initial catheter positioning and for elevating the catheter tip 32 off the surface of the bladder and more or less centering the tip within the bladder as it fills with infused fluid. The balloon 30 is located along the axis of the catheter at a distance from the tip that roughly centers the image acquisition component 28 within the average size filled bladder when the balloon 30 is seated at the bladder neck.

The sensors making up the image acquisition component may be fronted with lenses, and or mirror(s) designed for optimizing lighting, focus depth and field of view. The sensors, lighting and lens(es) combination will be designed and oriented to enable the capture of a panoramic view of at least 180 degrees in a plane of the longitudinal axis of the catheter. Ideally, this panoramic view may be seamless (or at least seamless when reconstructed digitally) and focused for optimal imaging of the mucosal surface being viewed. This panoramic view is such that a combination of simple axial longitudinal movements and axial rotation of the catheter without additional movement of the tip and without exchanging lenses or cameras will allow complete visualization of the mucosal surface of the interior of any expanded hollow viscus such as the lower urinary tract in a human subject.

In one embodiment, the catheter 22 is constructed with a bullet shaped tip of optically clear material is attached to the end of a multi-channel catheter extrusion during assembly. In addition to the image acquisition component 28 the tip may contain a laser fiber and/or ultrasound and or inertial sensors to aid in tracking orientation and position within the bladder. This tip may be connected via wires embedded during manufacture of the catheter or through a channel or lumen to the coupling portion 38B. The clear tip material may function as a lens or simply be a sealed cover for the sensors and lighting elements.

In the embodiment of FIGS. 1-3, the five sensors 28A-28E are within the sealed clear tip to create the necessary 180 degree plus panoramic view with sufficient directed lighting so that a single smooth but continuous (rather than stepwise) 360 degree catheter rotation may accomplish a complete examination of the mucosal surface in a fluid filled bladder (e.g. the inside of a sphere), once the catheter is properly positioned in the filled bladder with the catheter balloon inflated. A single 360 degree rotation of the catheter will be more than sufficient to image the entire interior of the bladder (assuming that the tip is sufficiently separated from the bladder wall). The images of each sensor/camera may also be isolated and reviewed separately using the console controls to simplify or emphasize an area during interpretation of the examination if desired.

Another arrangement may be used to obtain the panoramic view of at least 180 degrees in the axis of the catheter that includes looking straight backwards without requiring a Coude or bulbous tip and still allowing the surface for a backwards facing lens/sensor/camera. In particular, this arrangement makes use a "memory" curved shape of the catheter that can straighten out some as it passes through the urethra and then assumes a curved shape when floating free in a fluid filled bladder. This arrangement makes use of a catheter whose distal end portion has a substantial "off axis" deflection that is fixed in catheter memory, but will "straighten out" with the minor forces created by a relatively straight body channel such as the male urethra (the female urethra being so short as to not matter). Once inside a filled bladder, this deflection in combination with the array allows complete visualization of the bladder mucosal surface with a minimal set of external catheter manipulation(s) (e.g. simple catheter rotation).

The video monitor, recorder and control console unit 24 is located outside of the catheter and may be housed in a single or multiple housings. It may include software indicators and control functions and be powered by DC (battery) or AC electricity. It may also house a light source if fiber-optic lighting is used or a laser generator and optical device for measuring distance from the catheter tip to the bladder wall or other mucosal surfaces, e.g., to determine the volume of the filled bladder. The catheter and/or stylet may be connected to the monitor/controller/recorder by one or more cables and plugs or wireless connection in the case of a powered stylet or wireless transmitter with internal power supply.

Another embodiment of this invention, and which isn't shown in the drawing in the interest of drawing simplicity, contemplates use of an image acquisition component in the form of a sensor/camera and lens that may be on a pivot that is oriented perpendicularly to the axis of the catheter and is spring loaded to hold it in a look-forward position along the axis of the catheter. A string or wire actuator may be provided to cause the camera to rotate in an arc from looking forward to looking backward along the catheter axis while imaging through the clear sealed tip. This sensor/camera rotation may be actuated manually or by means of a mechanical actuator controlled by a control box connected at the external (proximal) end of the catheter. As the catheter is introduced through the urethra, the camera will typically be forward facing for visualizing the urethral mucosa circumferentially. Once positioned inside the bladder the balloon is inflated and seated at the bladder neck. The camera is then pivoted on its axis normal to the catheter axis while the catheter is held still and a panoramic strip image is obtained of the bladder wall from apex to base. A first panorama of a strip of bladder mucosa, like that shown in FIG. 5, may be imaged with the catheter oriented in the 12 o'clock position. The catheter may then be rotated sufficiently to image a second and immediately adjacent strip or sector of the mucosal surface. If the sensors have a 60 degree angular field of view, the catheter can be rotated to the 2 o'clock position to acquire the image of that immediately adjacent strip/sector. Then this same process is repeated stepwise at 4, 6, 8 and 10 o'clock positions to complete the full 360 degree digital imaging of the bladder (obviously with substantial image overlap at the apex and base). The catheter balloon is then deflated, the bladder emptied and the catheter removed to end the examination.

One method of use of the cytoscopic catheter 22 will now be described with reference to FIG. 2. To that end, a sterilized cystoscopic catheter, with or without a mechanical stylet in place, may be inserted transurethrally, i.e., through the urethra 16, into the patient using standard sterile bladder catheter insertion technique(s) and patient positioning (i.e. supine, lithotomy position, or any suitable position for urethral access). Optical and other communication and power cables in addition to fluid tubing may be connected to the catheter, typically prior to insertion especially for visualizing the male urethra, but may be done after insertion as well as may be most appropriate in females. Once the distal end portion (tip 32) of the catheter is in the bladder 10, the location of the catheter tip may be determined by viewing the image, laser rangefinder, ultrasound, or physical parameters, e.g., the seating of the inflatable balloon 30 at the bladder neck 14. A sterile fluid infusion source (e.g. a bag of sterile water, saline or other clear solution, elevated on an IV pole, or in a filled syringe, or in any reservoir connected to an infusion pump) may be connected to the fluid irrigation channel of the catheter via portion 38A of the coupling 38 to aid in insertion, visualization of the urethra during insertion, and subsequently to fill the bladder to facilitate the required visualization. A fluid volume monitor and or flow controls may be located within the control console unit 24, along with a separate pump or connected to sensors in the fluid path. Fluid volume in the catheter balloon 30, which is only filled after the catheter is fully inserted into the bladder, may also be monitored and controlled. If a powered stylet or other wireless transmitter is used instead of direct cabling from the control box, it may then be plugged in to the catheter at any time. Directional control and movement of the optics for a complete visualization of the bladder may be accomplished via any combination of simple catheter manipulations of longitudinal movement and catheter rotation, catheter balloon volume control, and/or controls built into or associated with the optics. In addition to real time imaging, software and hardware (e.g. sensors—both inertial and/or optical and fluid flow controls) may record, store and analyze the data from these movements to determine image orientation, fluid volumes, segmental viewing with or without mapping/identification, and when full visualization/examination has been completed. Visual presentation and review of the examination may be done in real-time and/or at a later time. The bladder may be emptied through the fluid channel prior to withdrawal of the catheter. In some clinical circumstances it also may be desirable to leave the catheter in place for continuous bladder drainage, and this is certainly an option available to the patient and user.

It is contemplated that the software in the unit 24 may be used to provide signals to the operator, in addition to real time images, regarding the camera(s) anatomic location and orientation on a visual monitor or by other means (e.g. sounds, alarms, language, lights, dial indicators, virtual bladder images and the like). Software indicators may also be used to provide direction and indicate completion of a satisfactory cystoscopic viewing/recording of the entire bladder interior. Fluid infusion and bladder volume monitoring may be tracked for purposes of the examination (e.g., it is often useful to know the bladder volume as the examination is being performed and have the patient note when he/she is feeling full to get a sense of his/her functional bladder capacity).

The specific choices for image acquisition component technology may be dictated by functional and/or cost constraints in addition to size constraints. It may be desirable to incorporate fiber-optics in the disposable catheter portion to optimize lighting, or to include tip location sensors in addition to the at least one lens of glass or plastic located near the tip for the at least one camera.

Other practical embodiments of these components are contemplated for the basic theme of allowing complete interior viewing of the bladder and urethra during simple insertion and rotation of a catheter.

The expandable positioning component 30 can be in the form of a petal-shaped, inflatable balloon, wherein the petals thereof are spaced from each other to create plural windows exposing portions of the mucosal surface of the bladder adjacent the neck of the bladder. In such an arrangement one or more channels or lumens can be provided through the catheter to fill the petals to effect optimal tip positioning. In fact, the expandable positioning component, may not be a balloon, but may be any type of expandable member mounted on the elongated member 26 which when expanded holds the tip 32 in the desired position away from any portion of the mucosal surface, yet which provides some window exposing a portion of the neck of the bladder and which can be rotated as a unit with the elongated member 26 through an arc of at least 360 degrees about the longitudinal axis of the insertion path, i.e., the IPA to effect the visualization of the entire mucosal surface of the bladder.

It should also be noted that other components than the imaging sensors described above may be used to form the image acquisition component. For example, it is contemplated that the image acquisition component may be in the form of one or more cameras (like the cytoscopic catheter 122 to be described) or optic fibers, each directed in a respective direction so that the composite field of view is at least 180 degrees to encompass a sector of the bladder's mucosal surface from the neck of the bladder to the mucosal surface opposite the neck of the bladder. The sensors/cameras used may have any field of view, but larger fields of view in a plane through or parallel to the axis IPA and greater range of focal depth are desirable for optimum performance and minimizing required catheter movement for completing an examination.

Turning now to FIGS. 10-21 the details of a more preferred embodiment of an instrument system 120 constructed in accordance with this invention for conducting a cystoscopic examination of a patient's bladder will now be described. The system 120 basically comprises a catheter endoscope (cystoscopy catheter) 122, the heretofore identified control console unit 24, and a power/control/data cable 110. The cable 110 serves to connect the catheter endoscope 122 to the console unit 24. The console unit 24 and the cable 110 are preferably reusable, while the catheter 122 is preferably a disposable device.

Figure 11:
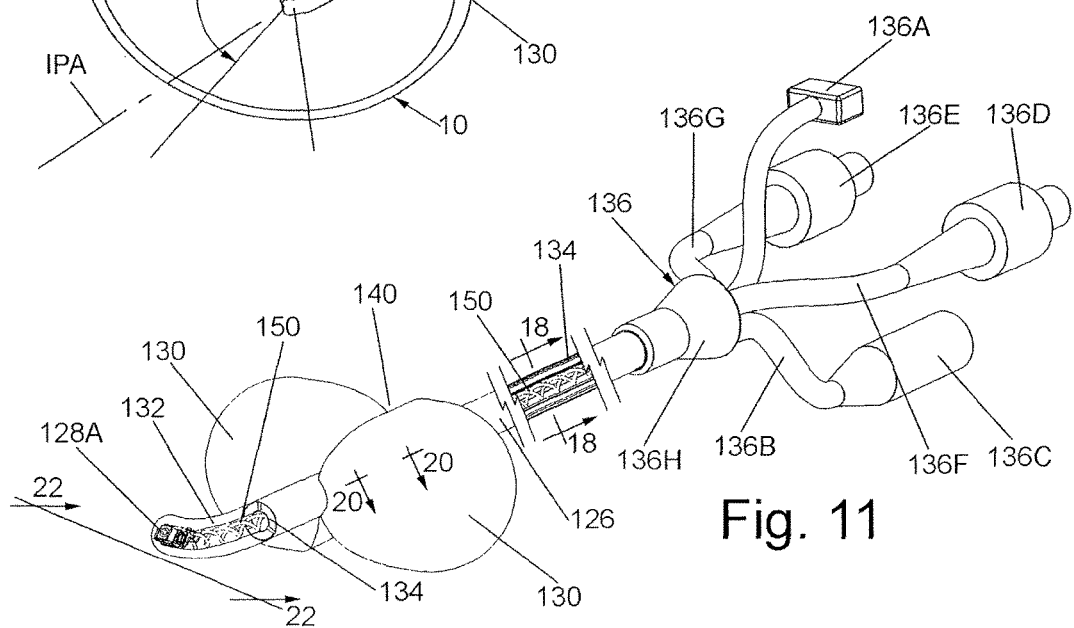
FIG. 11 is an isometric view, partially in section, of the catheter endoscope of FIG. 10, shown with its two positioning balloons inflated.
Figure 19:
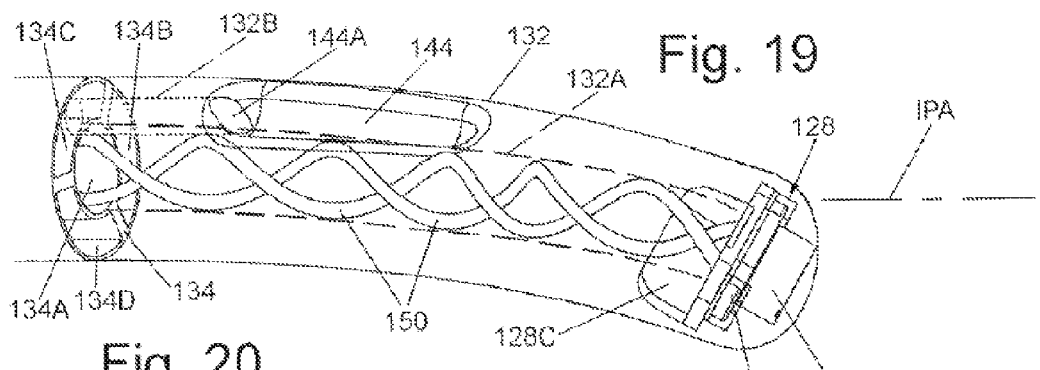
FIG. 19 is another isometric view of the distal end of the catheter endoscope shown in FIG. 11.
Figure 20:
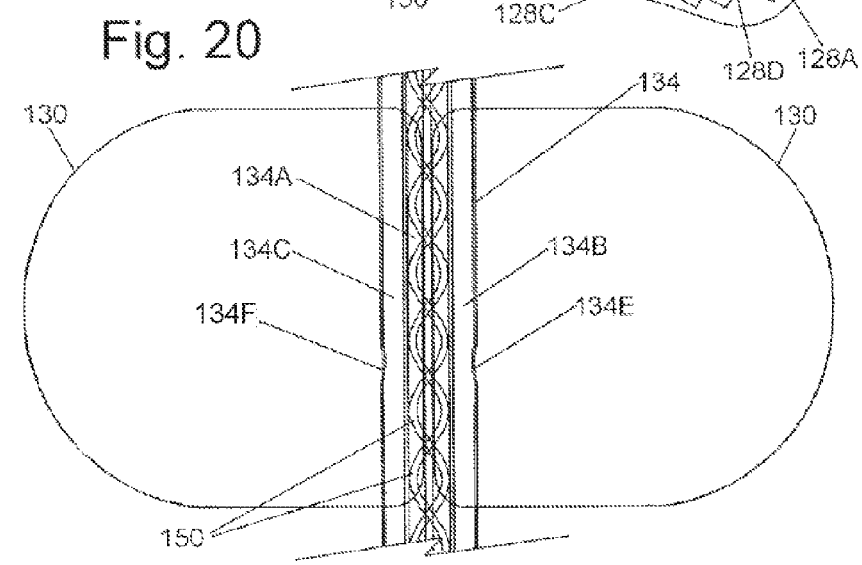
FIG. 20 is an enlarged sectional view taken along line 20-20 of FIG. 11 showing the ports for inflating the positioning balloons.
Figure 21:
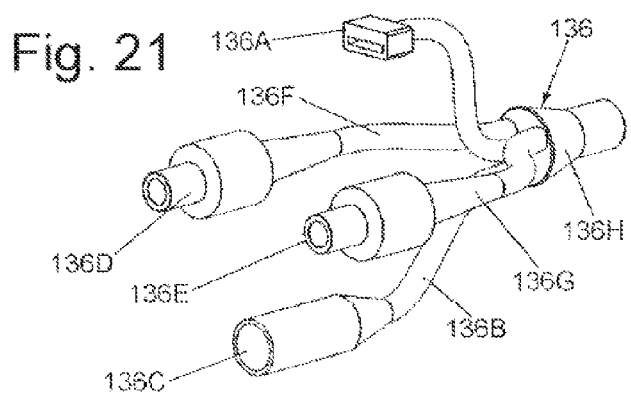
FIG. 21 is an isometric view of the proximal end portion of the catheter endoscope shown in FIG. 11.

The catheter 122 basically comprises an elongated catheter-like member 126, an image acquisition component 128 (FIGS. 12, 16, 17 and 19), and an expandable positioning component, e.g., a pair of inflatable balloons 130 (FIGS. 14, 15 and 20). The elongated catheter-like member 126 has a distal end portion or tip 132 in which the image acquisition component 128 (FIGS. 11, 12 and 19) is located, a tubular intermediate portion 134 (FIGS. 11, 13, 18, 20 and 21) and a proximally located coupling assembly 136 (FIGS. 11 and 21).

Figure 10:
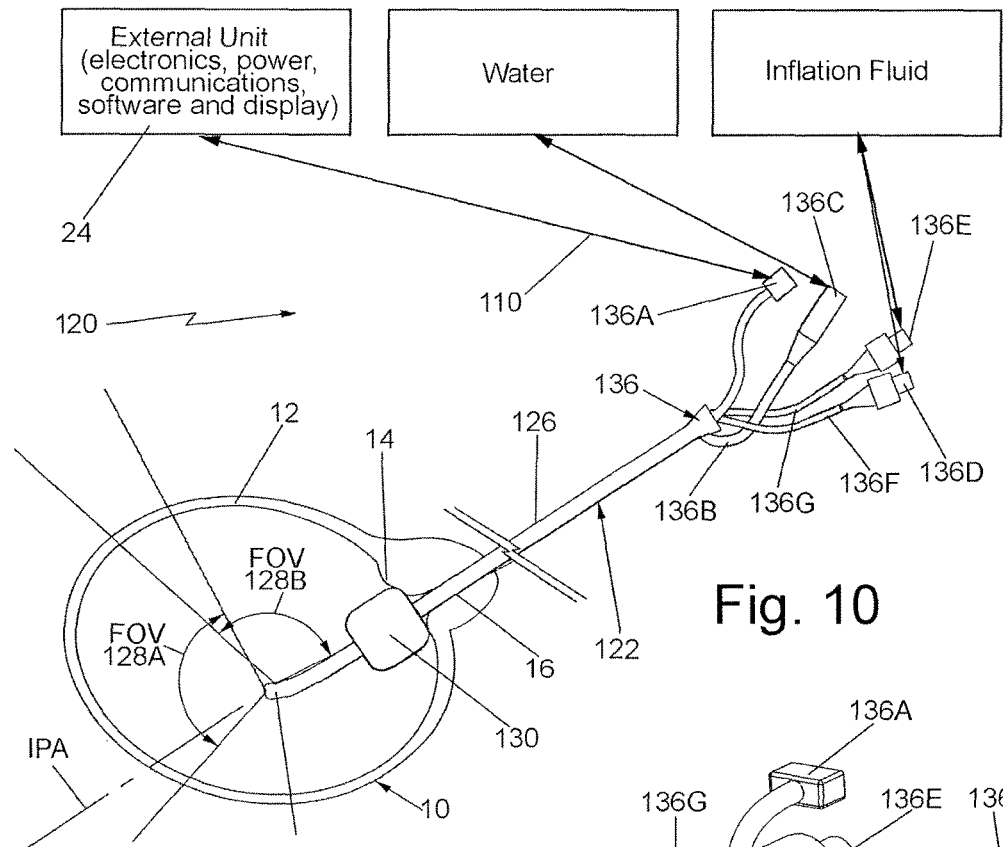
FIG. 10 is an illustration of another exemplary embodiment of a medical system making use of another exemplary and preferred catheter endoscope constructed in accordance with this invention.

Like the catheter endoscope 22, the catheter endoscope 122 is arranged to be introduced into the bladder 10 via an insertion path having a longitudinal axis IPA. The insertion path extends through the urethra 16 and the neck 14 of the bladder and has a longitudinal axis IPA which extends from the neck 14 of the bladder to the portion 42 of the mucosal surface 12 of the bladder directly opposite the neck of the bladder. The catheter 122 is constructed and arranged to be inserted to a desired longitudinal position along the axis IPA wherein the tip 132 is spaced away from any portion of the mucosal surface with the proximal surface of the balloons 130 in abutment with the neck of the bladder, as shown in FIG. 10. This tip position is also referred to as the 'desired longitudinal position" in which the tip is generally centered within the bladder.

In order to enable viable imaging of the mucosal surface of the bladder by the image acquisition component 128 the catheter 122 is constructed to enable it to introduce a sterile infusion or irrigation liquid, e.g., sterile water, into the bladder to fill the bladder. The catheter 122 is also arranged to have an inflation fluid introduced through it to inflate and deflate the balloons 130 and to have electrical power and electrical control and signals delivered through it between the image acquisition component 128 and the console unit 24.

To that end, the intermediate portion 134 of the elongated member 126 is a multi-lumen elongated member, which may be in the form of an extrusion of a standard length (e.g., about 40 cm overall), of approximately 18-20 French size, or less formed of any suitable flexible material. As best seen in FIGS. 13 and 18 the elongated member 134 includes a central passageway or lumen 134A, which is surrounded by three equally sized arcuate shaped lumens 134B, 134C and 134D. Each of the arcuate lumens 134B and 134C is arranged to carry a conventional balloon inflation fluid to a respective one of the balloons 130 to inflate the balloons, and when desired to deflate them (as will be described later). The arcuate lumen 134D is arranged to carry a sterile infusion or irrigation liquid, e.g., water, through it to a port 144A (FIGS. 12 and 19), to be described later, on the catheter's tip portion 132 so that the irrigation liquid can be introduced into the patient's bladder. The central lumen 134A serves to carry the electrical signal and power for the catheter's image acquisition component via a pair of electrical cables 150 extending therethrough. The catheter design with the relatively low stretch cabling in the center is desirable to allow the catheter to flex with equal resistance in all directions as much as possible. This allows the catheter tip to be rotated relatively smoothly and without sudden acceleration through some sectors because of unwanted spring-like motions.

The distal end of the intermediate portion 134 of the elongated member 126 is secured to the tip 132. In accordance with one exemplary preferred embodiment the tip 132 is bullet shaped to be atraumatic and is formed of an optically clear material, e.g., polycarbonate molded. The tip 132 serves to hold the image acquisition component 128 therein. The tip can be formed in various ways. For example, it can be molded as an integral unit about the image acquisition unit, so that the image acquisition unit is encapsulated therein, or can be formed of several components which can be secured together to form a unitary body in which the image acquisition unit is located with lenses on the surface. In any case, the proximal end of the tip 132 is fixedly secured to the distal end of the intermediate portion 134 of the elongated member 126 by any suitable means. In the embodiment shown the tip includes a central passageway 132A (FIGS. 12 and 19) in communication with the central passageway or lumen 134A of the intermediate portion 134 of the elongated member 126. It is through the passageway 132A that the distal end portions of the cables 150 from the central passageway 134A extend for electrical connection to the image acquisition component 128.

The image acquisition component 128 basically comprises a pair of solid state video cameras 128A and 128B, each having a large field of view (e.g., approximately 110 degrees or more) and which are fixedly mounted within the tip 132 via a mounting bracket 128C. In the exemplary embodiment shown in FIG. 10, the tip 132 is a Coude tip, i.e., it extends at an acute angle (e.g., 20 degrees) to the longitudinal axis of the member 126. As can be seen clearly in FIGS. 12 and 19 the camera 128A is angled in a distal direction and camera 128B angled in a proximal direction with respect to the longitudinal axis IPA to produce a combined panoramic field of view (FOV) extending longitudinally, i.e., along the longitudinal axis IPA for at least 180 degrees (e.g., approximately 210 degrees). This arrangement provides a panoramic image of a sector of the mucosal surface from the neck of the bladder to a point on the mucosal surface opposite the neck of the bladder within a predetermined angular field of view extending radially outward from the longitudinal axis of the insertion path similar to that provided by the catheter 22.

In order to illuminate the field of view of each of the cameras 128A and 128B, the image acquisition component 128 includes two pairs of LEDs 128D and 128E. The pair of LEDs 128D are mounted on the bracket 128B on opposite sides of the camera 128A and are directed such that they illuminate the field of view of that camera. In a similar manner, the other pair of LEDs 128E is mounted on the bracket 128B on opposite sides of the camera 128B and are directed such that they illuminate the field of view of that camera. The power for the LEDs and the cameras is provided via the cables 150. The control signals from the console unit 24 for the cameras and the LEDs are also provided via those cables. Data from the cameras representing the images acquired thereby are provided to the console unit via the cables 150. To that end, the proximal end of the cables 150 terminate at an electrical plug 136A (FIGS. 10, 11 and 21) forming a portion of the coupling assembly 136 and the power/control/data cable 110 includes a connector (not shown) which is arranged to be releasably connected to the plug 136A to electrically connect the catheter endoscope 122 to the console unit 24. In accordance with one preferred aspect of this invention, the cable 110 is reusable and can be cleaned. In use it will be covered with a sterile sleeve.

The cameras 128A and 128B can be of any suitable construction. One particularly suitable camera is a solid state video camera sold by Omnivision of Santa Clara, Calif. under the model designation OVM7695 VGA Camera Cube Chip. Each camera has its own associated lens. Since the tip 132 is formed of an optically clear material (or the lenses may be at the surface of the molding), the lenses of the cameras and the associated illuminating LEDs' are not obscured or otherwise by the material making up the tip so that the mucosal surface of the bladder can be illuminated by the LEDs and a good image thereof acquired by the cameras. If desired, the tip 132 may include openings or windows to the lenses and/or the LEDs. The LEDs can be of any suitable construction. One particularly suitable camera is an LED sold by Kingbright under the model designation APHK1608RWC/Z.

The two cameras 128A and 128B are oriented within the sealed clear tip to create the necessary 180 degree plus, e.g., 210 degree, panoramic view with sufficient directed lighting so that a single smooth but continuous (rather than stepwise) 360 degree catheter rotation may accomplish a complete examination of the mucosal surface in a fluid filled bladder (e.g. the inside of a sphere), once the catheter 122 is properly positioned in the filled bladder with the catheter's balloons 130 inflated, as will be described later. A single 360 degree rotation of the catheter will be more than sufficient to image the entire interior of the bladder (assuming that the tip is sufficiently separated from the bladder wall). The images of each camera may also be isolated and reviewed separately using the console controls to simplify or emphasize an area during interpretation of the examination if desired.

Another arrangement may be used to obtain the panoramic view of at least 180 degrees in the axis of the catheter that includes looking straight backwards without requiring a Coude tip and still allowing the surface for a backwards facing camera. In particular, the tip 132 may be constructed to make use a "memory" curved shape that can straighten out some as it passes through the urethra and then assumes a curved or otherwise angled shape when floating free in a fluid filled bladder. This arrangement makes use of a catheter whose distal end portion has a substantial "off axis" deflection that is fixed in catheter memory, but will "straighten out" with the minor forces created by a relatively straight body channel such as the male urethra (the female urethra being so short as to not matter). Once inside a filled bladder, this deflection in combination with the two cameras allows complete visualization of the bladder mucosal surface with a minimal set of external catheter manipulation(s) (e.g. simple catheter rotation).

In addition to the passageway 132A the tip 132 also includes another lumen or passageway 132B (FIGS. 12 and 19). The passageway 132B terminates at its distal end in the open port 144A and terminates at its proximal end in fluid communication with the lumen 124D of the member 134. Thus, the infusion liquid, e.g., water, introduced through the lumen 134D can flow through the passageway 132B and out through the port 144A to irrigate the bladder. In particular, the proximal end of the channel or lumen 134D in the member 134 is connected to a conduit 136B which terminates at a valve-less, dilated opening 136C of the coupling assembly 136. The opening 136C is configured to have for a friction type cone shaped connector (not shown) plugged therein. The cone connector is connected to a liquid source, e.g., a bag of sterile water on an elevated IV pole the bladder can be irrigated. With such an arrangement the sterile water can flow under the force of gravity from the bag, through the coupling assembly 136, through the channel or lumen 134D of the catheter and out through the port 144A into the bladder.

The construction and operation of the balloons 130 will be described in detail later. Suffice it for now to state that like the balloons 30, the balloons 130 are located proximally adjacent the tip 132 and are arranged when inflated to engage the mucosal surface 12 of the bladder 10 adjacent the neck 14 of the bladder. Thus, they serve to hold the catheter 122 in place in the bladder, while enabling it to be rotated about its central longitudinal axis. Like the balloons 30, the balloons 130 also define a window 140 (also to be described later) between them, with the predetermined angular field of view of the cameras 128A and 128B being aligned with the window 140 so that the balloons do not obscure or interfere with imaging of the mucosal surface adjacent the neck of the bladder by the proximally angled camera 128B.

Figure 22:
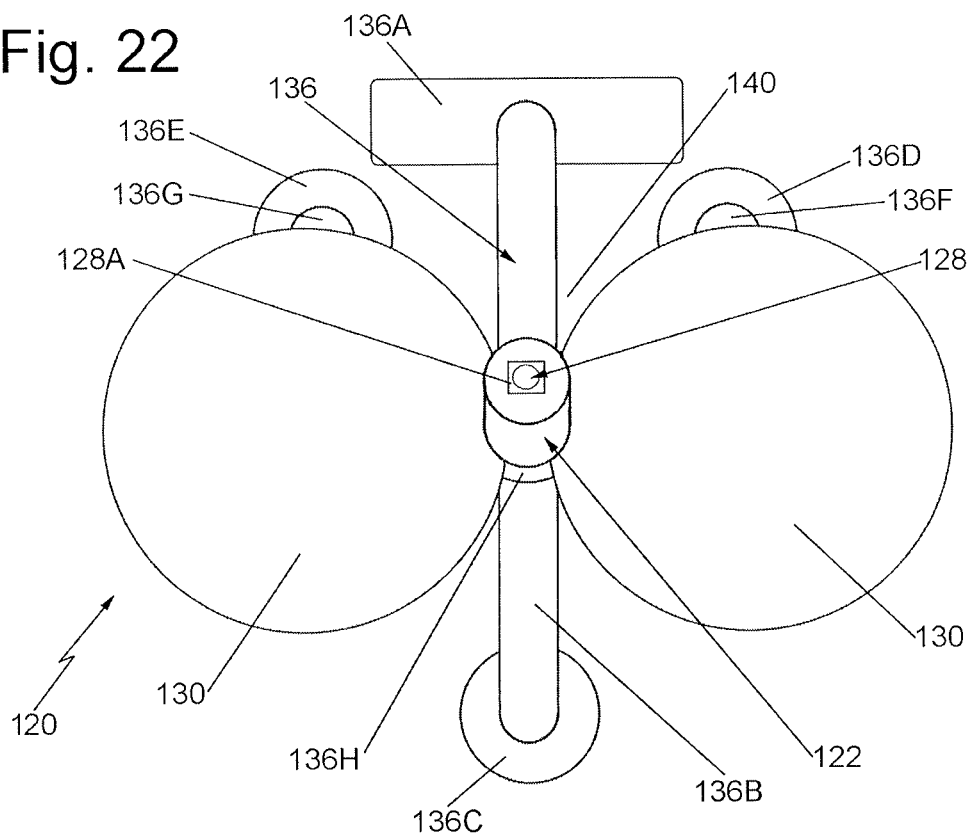
FIG. 22 is an end view taken along line 22-22 of FIG. 11.

Turning now to FIGS. 11, 14, 15, 20 and 22 the details of the balloons 130 will now be described. Each balloon 130 is a thin-walled member that is fixedly secured to the intermediate member 134 of the catheter 122 adjacent the tip 132. Other than their shape, the balloons 130 are of conventional construction. In particular, each balloon is a hollow member of a generally round shape when expanded and viewed from either the distal or proximal end thereof. As best seen in FIG. 14, each balloon includes a peripheral edge portion which includes a pair of linear side edges 130A and a pair of generally semi-circular end edges 130B. As best seen in FIG. 20, the intermediate member 134 of the catheter 122 includes a pair of inflation ports 134E and 134F. The port 134E is in fluid communication with the lumen or passageway 134B and the port 134F is in fluid communication with the lumen or passageway 134C. The side edges 130A and end edges 130B of one of the balloons 130 are fixedly secured to respective portions of the outer surface of the member 134 so that the hollow interior of that balloon is in fluid communication with the inflation port 134E. In a similar manner, the side edges 130A and end edges 130B of the other one of the balloons 130 are fixedly secured to respective portions of the outer surface of the member 134 so that the hollow interior of that balloon is in fluid communication with the inflation port 134F. With the balloons 130 being secured to the member 134 of the catheter as just described, the space between the balloons at that member forms the heretofore mentioned window 140. As can be seen in FIG. 22 the window 140 is of a generally arcuate V-shape, flaring outward from the member 134. Since the catheter 122 has to be able to look backward, the space between the balloons, e.g., the V-shaped space or window 140, is preferably made as large as possible, particularly at the apex of the V.

The inflation/deflation of the balloons 130 is accomplished via a pair of conventional luer valve fittings 136D and 136E and respective conduits 136F and 136G forming a portion of the coupling assembly 136. In particular, the proximal end of the inflation/deflation passageway 134B is connected to the distal end of the conduit 136F. The proximal end of that conduit is connected to the luer fitting 136D. In a similar manner the proximal end of the inflation/deflation passageway 134C is connected to the distal end of the conduit 136G. Each luer fitting is arranged to be connected to a source of conventional inflation fluid provided by a syringe (not shown). Thus, when the inflation fluid is introduced into the luer fitting 136D by the syringe, it flows through the associated conduit 136F through the associated passageway 134B in the intermediate member 134 and out through the port 134E to inflate its associated balloon 130. Similarly, when the inflation fluid is introduced into the luer fitting 136E by the syringe, it flows through the associated conduit 136F through the associated passageway 134C in the intermediate member 134 and out through the port 134F to inflate its associated balloon 130.

The acquisition of the image of the entire mucosal surface of the bladder is accomplished by rotating the catheter 122 about the axis IPA of the insertion path once the catheter is in the desired longitudinal position such as shown in FIG. 10. This action is accomplished by manipulating (rotating) a hub portion 136H of the coupling assembly 136 so that the portion of the catheter within the bladder, including the balloons 130, rotates about the axis IPA. Since the balloons 130 rotate as a unit with the catheter about the axis IPA, the window 140 of the balloons will rotate simultaneously with the rotation of the image acquisition component, e.g., the cameras 128A and 128B, at the tip 132 to ensure that the mucosal surface at neck of the bladder will not be obscured by the balloons at any point during the 360 degree rotation of the catheter about that axis.

As should be appreciated by those skilled in the art the angular field of view of each of the cameras 128A and 128B is not critical since the catheter 122 is rotated about the longitudinal insertion axis IPA through an arc of at least 360 degrees while its tip 132 is in the desired longitudinal position along that axis to provide a composite image of the entire mucosal surface of the bladder. It should be noted that in practice the respective fields of view of each of the cameras 128A and 128B will overlap each other as shown in FIG. 10 to provide a desired depth of field to viably image the mucosal surfaces at which the respective cameras are aimed. The desired amount of overlap for optimal imaging is accomplished by ensuring that the two fields of view start to overlap at less than 2 cm from the tip. Moreover, the catheter and its image acquisition component is arranged so that the cameras look past the catheter centerline looking both forward (distally) and backwards (proximally) to allow or compensate for some catheter flex, and has sufficient field of view looking forward in axis IPA to allow for circumferential visualization of the male urethra during insertion.

Software in the system 120 utilizes the fields imaged by each camera to digitally process the electrical signals representative of the imaged fields to register or stitch those fields together (e.g., to "edge-match" them) to form the desired composite image. Thus, with the system of this invention the user can view a portion or the entirety of the mucosal surface of the bladder. Overlap of the visual fields is not important as long as all mucosal surfaces are visualized. However, it may be practical to present the images as seamless using pure software pixel image analysis or other, approaches to image registration.

The console unit 24 is arranged for visually displaying video images acquired by the catheter 122. Those images may be of the entire mucosal surface of the bladder, the urethra or any portion of either. Moreover, the images may be displayed as still images, if desired. To that end, the unit 24 includes a video recorder (not shown) to record the data representing the images provided by the catheter. The console unit includes a touch screen 24A and an associated display coupled to the touch screen. The unit 24 can display the recorded data from each imaging sensor at a later time in any format desired by the reviewer. Thus the images may be reviewed as a panoramic movie, as a movie from each individual camera, as still panoramic images from selected sectors obtained during catheter rotation or as individual sector camera images. To that end, the unit 24 includes various electronic circuitry and components, e.g., a microprocessor, fluid management components, sensor monitors and software to assist with the examination and for controlling the operation of the various components of the system and reviewing the image data. The monitor screen may be a touchscreen that allows the user to digitally scroll through the images and stop where desired. Electric power for the console unit 24 may be by means of a conventional power cord. Alternatively, or in addition, the unit 24 may include an on-board power supply, e.g., a battery.

The console unit 24 may also arranged to control and monitor the volume of fluid provided to the balloons 130, thereby controlling separation of the catheter distal end (tip) off (away from) the mucosal surface of the bladder once the catheter is through the urethra and correctly located in the bladder as shown in FIG. 10. The console unit 24 is also arranged control of the optics, such as the intensity of the light provided by the LEDs, and the focus and/or selection of the cameras 128A and 128B.

Like the catheter 22, the catheter 122 may also include position sensors incorporated in or near the tip and a laser rangefinder. An additional channel, which is blind-ending, may be provided in a segment of the catheter that does not enter the patient, for forming a self-sealing receptacle. This channel with the sealed end may receive a plug-in removable stylet that may communicate with power, lighting, data cables, camera(s) and/or sensors near the tip. Also, batteries may be embedded in the catheter wall and connected to LEDs and/or the cameras. As mentioned earlier AC or DC power (as the case may be) and data communication are supplied via the cables 150 incorporated in the catheter.

As shown in FIGS. 10-12 and 19 and as mentioned above the catheter 122 preferably has a Coude tip 132. However, that tip may be of different shape provided it accommodates a backward looking camera, e.g., camera 128B, so that the portion of the interior of the bladder at the bladder's neck is not obscured or otherwise blocked by the balloons 130.

It is anticipated that but for the inclusion of the expandable balloons 130 the tip 132 of the catheter 22 may not routinely end up in a position in the bladder that is ideal for panoramic viewing of the entire mucosal surface at all angles of rotation of the catheter. For example, the tip 132 could end up resting in contact with the posterior wall of the bladder. The optics, light distribution and cameras, rely on a clear fluid interface and adequate separation from the mucosal surface for optimal viewing. This is where the balloons 130 assist by holding the catheter in the desired longitudinal position. In this regard, inflating the balloons will be useful for initial catheter positioning and for elevating the catheter tip 132 off the surface of the bladder and more or less centering the tip within the bladder as it fills with infused fluid. The balloons 130 are located along the axis of the catheter at a distance from the tip 132 that roughly centers the image acquisition component 128 within the average size filled bladder when the balloons 130 are seated at the bladder neck.

The video monitor, recorder and control console unit 24 is located outside of the catheter 122 and may be housed in a single or multiple housings. It may include software indicators and control functions and be powered by DC (battery) or AC electricity. It may also house a light source if fiber-optic lighting is used in lieu of the LEDs. A laser generator and optical device for measuring distance from the catheter tip to the bladder wall or other mucosal surfaces, e.g., to determine the volume of the filled bladder can also be provided in the console unit.

One preferred method of use of a cytoscopic catheter 122 constructed in accordance with this invention will now be described with reference to FIG. 10 and may vary slightly between men and women. In men the water connection to the catheter must be made prior to catheter insertion. This is so that, like traditional cystoscopy, the water can be running during insertion of the instrument so that full visualization of the urethra is accomplished. This is not necessary in women. In either case the patient is ideally in the supine or modified lithotomy position on a flat bed or table. The patient is prepped and anesthetic lubricant is injected into the urethra. The connector 136C of the catheter's coupling assembly 136 is connected to a fluid irrigation source, e.g., a bag of sterile water, saline or other clear solution, elevated on an IV pole, or in a filled syringe, or in any reservoir connected to an infusion pump. The luer connectors 136D and 136E of the catheter's coupling assembly 136 are connected to a source of inflation fluid, e.g., a fluid filled syringe. The cable 110 from the console unit 24 is connected to the plug of catheter's coupling assembly. Once that has been accomplished the catheter can be inserted into the patient using standard technique with everything "on". In particular, when the operator starts inserting the catheter in the patient with the clear infusion liquid on, it will expand the patient's urethra to facilitate insertion. Moreover, the running infusion liquid water enables the visualization of the insertion path through the patient. For example if the instrument is being used on a man the operator will want to be able to see the urethra, the sphincter, and the prostate. Those images are provided by the image acquisition unit as the catheter is being inserted, are viewable on the console's monitor and are recorded. Once the catheter is fully inserted, the catheter's balloons 130 are inflated from the fluid filled syringe and the catheter is pulled back so that the balloons gently engage the bladder's neck. The bladder is preferably filled completely or at least to a comfortable degree with the infusion liquid so that there are no folds in it to be able to visualize its entire inner surface. The catheter is then slowly rotated 360 degrees in either direction over approximately a ten second interval to view the entire mucosal surface and record the data from the cameras for later viewing and study to the extent desired.

In addition to real time imaging, software and hardware (e.g. sensors—both inertial and/or optical and fluid flow controls) may be included in the console unit 24 to record, store and analyze the data from these movements to determine image orientation, fluid volumes, segmental viewing with or without mapping/identification, and when full visualization/examination has been completed.

Figure 23:
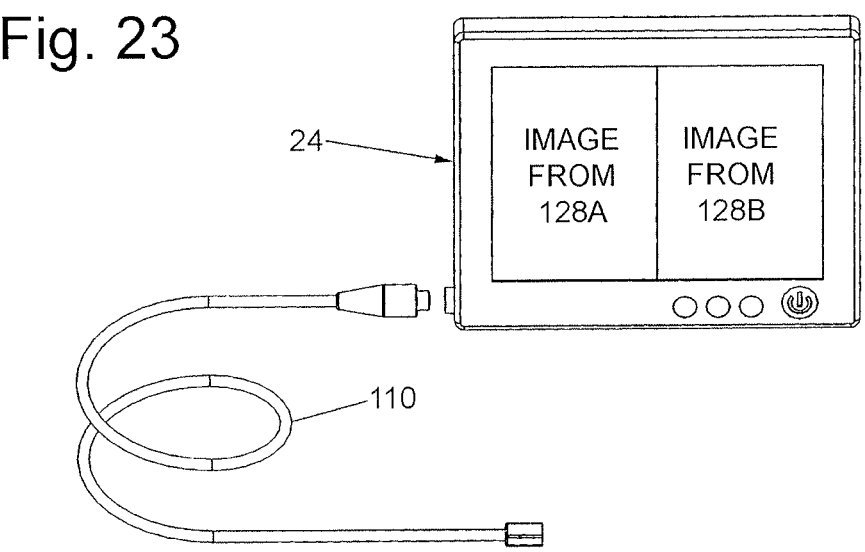
FIG. 23 is a front elevation view of the console unit of the system of FIG. 10 and its associated cable for connecting the console unit to the catheter endoscope.

FIG. 23 shows one exemplary embodiment of the console unit 24 and its associated cable 110. The monitor includes a touch screen display panel of any type suitable, LCD, LED, OLED, etc. The touch screen display is arranged to provide a "panoramic view" of the bladder that is achieved with the 110 degree view from each camera. To that end, as shown in FIG. 23 the image provided by the two cameras are displayed side-by-side, e.g., the image provided by camera 128A is shown on one side of the screen and designated "image from camera 128A", while the image provided by camera 128B is shown on the other side of the screen and designated "image from camera 128B". The images are presented in this side-by-side format and always shown together in the same axis and facing in the same radian (i.e., images locked in the same axis of the catheter and viewed as if from the side of the catheter behind the cameras FOV). Since the screen is a touchscreen it allows the viewer to scroll clockwise or counterclockwise around the axis of the catheter.

After imaging of the bladder has been completed by the system 120, the bladder can be drained through the recess 144, the associated port 144A, the associated passageway 132B in the tip 132 into the passageway 134D and from there through the conduit 136B and associated connector 136C out of the catheter. Once that has been accomplished the catheter can be removed. The reusable cable 110 can be disconnected from the catheter 122 so that the catheter and all other disposable components of the system 120 can be discarded. Alternatively, the catheter could be left in pace if continued urinary drainage is desired.

It is contemplated that the software in the unit 24 may be used to provide signals to the operator regarding the camera(s) anatomic location and orientation on a visual monitor or by other means (e.g. sounds, alarms, language, lights, dial indicators, virtual bladder images and the like). Software indicators may also be used to provide direction and indicate completion of a satisfactory cystoscopic viewing/recording of the entire bladder interior. Fluid infusion and bladder volume monitoring may be tracked for purposes of the examination (e.g., it is often useful to know the bladder volume as the examination is being performed and have the patient note when he/she is feeling full to get a sense of his/her functional bladder capacity). Moreover, the construction of the console, e.g., the inclusion of a video recorder, permits visual presentation and review of the examination to be accomplished at a later time in addition to or in lieu of real-time review. Software in the console may be able to read the serial number of the individual catheter being use and have a mechanism that prevents re-use. Similarly the catheter may have an identifying component that may be altered by communication with the software in the monitor to prevent re-use.

Figure 24:
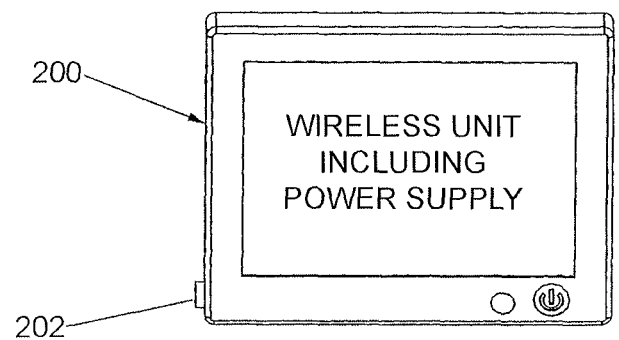
FIG. 24 is a front elevation view of an optional wireless transmitter and power supply unit that may be used to power the catheter endoscope of FIG. 1 and wirelessly transmit electrical signals representative of the images acquired by that catheter to the console unit.

The catheter endoscope 122, like the catheter endoscope 22, may be constructed to eliminate the need for a cable, like cable 110, to connect it to the console unit 24. For example, as shown in FIG. 24 an optional wireless transmitter and power supply unit 200 may be included as part of the system 120. In such a case the unit 200 can be in the form of a small box including a self-contained power supply (not shown), e.g., battery, and wireless transmitter (not shown) which are arranged to be electrically connected to the electrical components of the catheter endoscope 122 via an electrical receptacle 202 forming a portion of the unit 200. The receptacle 202 is arranged to receive the plug 136A of the catheter endoscope 122. Thus, when the plug of the catheter is connected to the receptacle 202 electrical power will be provided to operate the catheter's electrical components and its wireless transmitter. The wireless transmitter serves to transmit electrical signals representing the images acquired by the image acquisition component to an appropriate wireless receiver in the console unit 24. If desired, the unit 200 may include a wireless transceiver (i.e., wireless transmitter and wireless receiver) so that control signals for operating the catheter 122 can be wirelessly transmitted to the transceiver by the console unit 24. In such a case the console unit will also include a wireless transceiver. The unit 200 is preferably reusable and thus can be provided with a sterile pouch cover (not shown).

As discussed with reference to the catheter endoscope 22, the expandable positioning component of the catheter 122 can be in the form of a petal-shaped, inflatable balloon, in lieu of the two balloons 130 shown and described above. Other changes in the catheter are contemplated. Thus, it should be understood that while the embodiment 122 is deemed a preferred embodiment of the invention, changes can be made to it within the scope of this invention that have not be mentioned heretofore. For example, the catheter may include a Teflon® coating on it to make it more slippery to facilitate insertion and manipulation within the bladder. The balloons 130 can be attached to the intermediate part 134 (e.g., the extrusion) separately or may be in the form of an overlay. The tip 132 and the intermediate portion 134 may be formed, e.g., molded, as an integral unit in lieu of separate units which are secured together. While the preferred embodiment of the catheter is pre-sterilized and packaged for single use, that needn't be the case. Thus, if desired the catheter can be made so that it is reusable. Moreover, in the exemplary embodiment of catheter 122 the cable (wiring) for the cameras and LEDs is provided via the center channel or lumen 134A, that is of considerable importance, although not mandatory, because the catheter needs to be able to rotate smoothly (without lurching), as it might not if there was a lot of asymmetry to the bending force/resistance in the catheter (since in men at least, the catheter will obtain the panoramic video during rotation with at least one significant bend in the catheter). This is also why the cables 150 are twisted into a spiral as shown. It should be noted that while the figures of the drawing show only a twisted pair of cables there may be any number of separate small electrical wires, e.g., eight, that provide power to the LEDs and cameras as well as video data transmission.

As should be appreciated by those skilled in the art from the foregoing the systems of this invention should result in a change in the cystoscopy paradigm. Heretofore, all current cystoscopes essentially mimic the standard reusable versions as closely as possible with some variations that pursue the goals of eliminating or reducing reprocessing costs and improving sterility. The systems of this invention achieve those goals, but go much farther by also eliminating the requirement for a skilled operator, a specialty venue and scheduling logistics. In particular, catheters constructed in accordance with this invention utilize the self-directing nature of a typical urinary catheter to safely introduce the optical components into the bladder and thus eliminate the bottleneck requirement of a specialty trained physician operator, sterile equipment and a special room/setup/venue. The systems of this invention allow for a complete diagnostic examination to be performed by anyone with sufficient training/skill to perform sterile bladder catheterization. The rote nature of the procedure and video analytics eliminate the skills required for ascertaining when the examination is complete. Video recording allows real time or retrospective documentation of a complete examination of the bladder interior, and preserves the findings indefinitely. While an urologist may still be required to interpret the examination, this may be done remotely or at least at a most convenient time to facilitate workflow and reduce cost. One of the many advantages of the systems of this invention is the ability to atraumatically accomplish a complete diagnostic cystoscopy at any time, in almost any place with almost any skill level of operator. The systems of this invention allow cystoscopy to be performed by a nurse or technician with minimal training, in any location, without the need for sterilization equipment, or even external power. The urologist can save the time it takes to perform the procedure, efficiently view and share the images (similar to a radiologist) at an optimum time and place, and avoid the expense associated with the universal equipment and logistical issues that are currently integral to cystoscopy.

All the instantaneous skills required for typical cystoscopy: 1) familiarity with the normal male and female lower urinary tract anatomy in the collapsed and expanded conditions; 2) the technical knowledge of the equipment and its use and limitations; 3) the ability to navigate the instrument past urethral anatomic landmarks (especially relevant in male patients); 4) the ability to position and manipulate the cystoscope for complete bladder viewing (a known source of error and malpractice litigation); and 5) the recognition of all varieties of anatomic pathology, are delayed or eliminated for convenience by this system.

Therefore, it is anticipated that this invention will allow cystoscopy to be performed more easily (reduced skill level required), more expeditiously (any time), more cheaply (considering global costs), more reliably (fewer missed lesions), more safely (reduced risk of infections from inadequate cleaning and sterilization), and more comfortably for the patient than current practice methods allow.

Without further elaboration the foregoing will so fully illustrate my invention that others may, by applying current or future knowledge, adopt the same for use under various conditions of service.

I claim:

1. A catheter endoscope for deployment in the body of a patient to provide an image of the mucosal surface of the patient's bladder for display on an externally located display device, said catheter endoscope comprising:
    an elongated member,
    an image acquisition component, and
    an expandable positioning component,
    said elongated member having a distal end portion at which said image acquisition component is located,
    said expandable positioning component being located proximally adjacent said distal end portion, said distal end portion and said expandable positioning component being arranged to be deployed in the bladder by moving said elongated member and said expandable positioning component through the urethra and the neck of the bladder along an insertion path towards the mucosal surface of the bladder opposite the neck of the bladder whereupon said distal end portion is located at a desired longitudinal position along said insertion path and said expandable positioning component is located adjacent the neck of the bladder, said insertion path having a longitudinal axis,
    said expandable positioning component being configured to be expanded to hold said distal end portion of said elongated member in said desired longitudinal position and away from any portion of the mucosal surface of the bladder,
    said expandable positioning component having a window therein exposing a portion of the mucosal surface of the bladder contiguous with the neck of the bladder,
    said image acquisition component being configured to acquire a panoramic image of a sector of the mucosal surface of the bladder from the neck of the bladder to the mucosal surface of the bladder opposite the neck of the bladder within a predetermined angular field of view extending radially outward from the longitudinal axis of the insertion path, said window being located within said predetermined angular field of view so as to expose a portion of the mucosal surface of the bladder contiguous with the neck of the bladder within said sector of the mucosal surface,
    said elongated member being configured to be rotated about the longitudinal axis of the insertion path while said distal end portion of said elongated member is in said desired longitudinal position whereupon said image acquisition component acquires a video image of the mucosal surface of the bladder from the neck of the bladder to the mucosal surface of the bladder opposite the neck of the bladder, and
    said catheter endoscope being configured to provide said video image to the externally located display device.

2. The catheter endoscope of claim 1 wherein said distal end portion of said elongated member is arranged to extend at an acute angle to the longitudinal axis of the insertion path.

3. The catheter endoscope of claim 2 wherein said distal end portion of said elongated member is arranged to be oriented generally coaxially with the longitudinal axis of the insertion path to facilitate insertion of said catheter endoscope through the urethra and the neck of the bladder into the bladder.

4. The catheter endoscope of claim 1 wherein said elongated member comprises a lumen extending therethrough for receipt of a liquid.

5. The catheter endoscope of claim 4 wherein said lumen includes an outlet in said elongated member for infusing the liquid into the bladder.

6. The catheter endoscope of claim 1 wherein said expandable positioning component comprises an inflatable balloon.

7. The catheter endoscope of claim 6 wherein said balloon includes at least one portion which extends about only a portion of the periphery of said elongated member to form said window.

8. The catheter endoscope of claim 7 wherein said elongated member comprises a first lumen extending therethrough in fluid communication with said balloon for receipt of a fluid to inflate said balloon.

9. The catheter endoscope of claim 8 said elongated member comprises a second lumen extending therethrough for receipt of a liquid, said second lumen including an outlet for infusing the liquid into the bladder.

10. The catheter endoscope of claim 9 wherein said elongated member comprises a third lumen through which an electrical conductor extends, said electrical conductor being coupled to said image acquisition component to provide the video image to the externally located display device.

11. The catheter endoscope of claim 6 wherein said elongated member comprises a lumen extending therethrough in fluid communication with said balloon for receipt of a fluid to inflate said balloon.

12. The catheter endoscope of claim 1 wherein said image acquisition component comprises at least two image sensors, each of said image sensors being directed to a respective portion of the sector of the mucosal surface from the neck of the bladder to the mucosal surface of the bladder opposite the neck of the bladder to acquire an image of its respective portion of the sector of the mucosal surface.

13. The catheter endoscope of claim 12 wherein the at least two image sensors comprises five image sensors.

14. The catheter endoscope of claim 12 additionally comprising at least two sources of illumination, each of said sources of illumination being configured for illuminating a respective portion of the sector of the mucosal surface from the neck of the bladder to the mucosal surface of the bladder opposite the neck of the bladder.

15. The catheter endoscope of claim 14 wherein each of said image sensors comprises a lens, each of said lenses being directed to a respective portion of the sector of the mucosal surface from the neck of the bladder to the mucosal surface of the bladder opposite the neck of the bladder.

16. The catheter endoscope of claim 1 additionally comprising a source of illumination for illuminating at least a portion of the predetermined angular field of view.

17. The catheter endoscope of claim 1 wherein said elongated member is flexible.

18. The catheter endoscope of claim 1 wherein said catheter endoscope is pre-sterilized and packaged for single use.

19. The catheter endoscope of claim 1, wherein the expandable positioning component comprises a first expandable balloon and a second expandable balloon, wherein the first and second expandable balloons are located adjacent the elongated member.

20. The catheter endoscope of claim 19, wherein the first expandable balloon and second expandable balloon are coupled to the elongated member and a space between the first and second expandable balloons defines the window and provides the predetermined angular field of view for the image acquisition component.

21. The catheter endoscope of claim 19, wherein the window comprises a V-shaped window extending outwardly from the elongated member.

22. The catheter endoscope of claim 1, wherein the elongated member comprises a plurality of lumens and the expandable positioning component comprises a first balloon and a second balloon.

23. The catheter endoscope of claim 22, wherein the plurality of lumens comprises:
a first lumen configured to supply a fluid to the first balloon to inflate the first balloon, and
a second lumen configured to supply a fluid to the second balloon to inflate the second balloon.

24. The catheter endoscope of claim 23, wherein the plurality of lumens comprises:
a third lumen configured to supply power to the image acquisition component.

25. The catheter endoscope of claim 1, wherein the image acquisition component comprises a first camera and a second camera, wherein the first and second cameras are located in the distal end portion of the elongated member and provide at least a 180 degree field of view.

* * * * *